United States Patent [19]

Peery et al.

[11] Patent Number: 5,786,463

[45] Date of Patent: Jul. 28, 1998

[54] **MULTIPLE DRUG RESISTANCE GENE OF *CRYPTOCOCCUS NEOFORMANS***

[75] Inventors: Robert Brown Peery, Brownsburg; Paul Luther Skatrud; Susan Jane Thornewell, both of Indianapolis, all of Ind.

[73] Assignee: Eli Lilly and Company, Indianapolis, Ind.

[21] Appl. No.: 612,521

[22] Filed: Mar. 8, 1996

[51] Int. Cl.$^6$ .......................... C07H 21/04; C12P 21/02; C12N 5/10

[52] U.S. Cl. .................. 536/23.1; 435/69.1; 435/325; 435/375

[58] Field of Search ................ 536/23.1; 435/320.1, 435/254.11, 69.1, 325, 375; 530/395

[56] References Cited

U.S. PATENT DOCUMENTS 5,516,655  5/1996  Peery et al. ........................ 435/69.1

OTHER PUBLICATIONS

Fojo, A. et al., 1987, Proc. Natl. Acad. Sci. USA 84:265–269.
Gottesman, M. and Pastan, L., 1993, Annu. Rev. Biochem. 62:385–427.
Pastan, I. and Gottesman, M., 1991, Annu. Rev. Med. 42:277–286.
Pastan, I. and Gottesman, M., 1987, New Eng. J. of Med. 316(22):1388–1393.
Gottesman, M. and Pastan, L., 1988, J. of Biol. Chem. 263(25):12163–12166.
Raymond, M. et al., 1994, Mol. and Cell. Biol. 14(1):277–286.
Ruetz, S. et al., 1993, Proc. Natl. Acad. Sci. USA 90:11588–11592.
Raymond, M., et al., 1992, Science 256:232–234.
Parkinson, T. et al., 1995, Antimicrobial Agents and Chemotherapy, 39 (8): 1696–1699.
Katzmann, D.J. et al., 1995, Molecular and Cellular Biology, 15(12): 6875–6883.
Balzi, E. et al., 1995, Journal of Bioenergetics and Biomembranes, 27(1): 71–76.
Hirata D., et al., 1994, Current Genetics, 26: 285–294.
Balzi, E. et al., 1994, Biochimica et Biophysica Acta, 1187: 152–162.
Bissinger P.H., et al., 1994, Journal of Biological Chemistry, 269 (6): 4180–4186.
Ben-Yaacov, R., et al., 1994, Antimicrobial Agents and Chemotherapy, 38(4): 648–652.
Mitchell-Olds, T., et al, 1995, Heredity, 75: 362–369.

*Primary Examiner*—Nancy Degen
*Assistant Examiner*—Matthew Latimer
*Attorney, Agent, or Firm*—Amy E. Hamilton; David E. Boone

[57] ABSTRACT

The invention provides isolated nucleic acid compounds encoding a multiple drug resistance protein of *Cryptococcus neoformans*. Vectors and transformed host cells comprising the multiple drug resistance-encoding DNA of *Cryptococcus neoformans* CneMDR1 are also provided. The invention further provides assays which utilize these transformed host cells.

11 Claims, 2 Drawing Sheets

Figure 1. Restriction site and function map of plasmid pPST4

Figure 2. Restriction site and function map of plasmid pPST5

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 4224 base pairs
( B ) TYPE: nucleic acid
( C ) STRANDEDNESS: double
( D ) TOPOLOGY: linear ( i x ) FEATURE:
( A ) NAME/KEY: CDS
( B ) LOCATION: 1..4224

( x i ) SEQUENCE DESCRIPTION: SEQ ID NO:1:

| ATG | TCT | GCT | TCT | CCA | GGA | CTC | ACT | GCG | GCT | GCA | GCC | GGC | CCC | GAC | CAT | 48 |
| Met | Ser | Ala | Ser | Pro | Gly | Leu | Thr | Ala | Ala | Ala | Ala | Gly | Pro | Asp | His | |
| 1 | | | | 5 | | | | | 10 | | | | | 15 | | |

| CTT | CAA | GCC | CGC | CGT | GAC | GAA | AAA | GTC | ATC | GAC | TCC | GAG | AAG | GAT | GCT | 96 |
| Leu | Gln | Ala | Arg | Arg | Asp | Glu | Lys | Val | Ile | Asp | Ser | Glu | Lys | Asp | Ala | |
| | | | 20 | | | | 25 | | | | | 30 | | | | |

| CTT | GCC | CAC | GAT | GCT | CAT | GCT | GTG | AAC | TCT | GGT | ATA | CCT | TAC | CCA | ACA | 144 |
| Leu | Ala | His | Asp | Ala | His | Ala | Val | Asn | Ser | Gly | Ile | Pro | Tyr | Pro | Thr | |
| | | 35 | | | | 40 | | | | | 45 | | | | | |

| GCC | ACT | GCA | CCT | AAT | GTC | GGA | GCA | CCC | ACT | GTC | CCA | ATC | AGC | GTT | GGT | 192 |
| Ala | Thr | Ala | Pro | Asn | Val | Gly | Ala | Pro | Thr | Val | Pro | Ile | Ser | Val | Gly | |
| | 50 | | | | | 55 | | | | | 60 | | | | | |

| CGC | GTT | TCG | TCG | GCA | GCC | GAA | GGA | AAG | ATT | AGC | CGC | TCC | TCT | ATC | GCC | 240 |
| Arg | Val | Ser | Ser | Ala | Ala | Glu | Gly | Lys | Ile | Ser | Arg | Ser | Ser | Ile | Ala | |
| 65 | | | | | 70 | | | | | 75 | | | | | 80 | |

| GCT | TCC | TCT | GAC | ACT | CTC | CGC | AAC | TCT | CCG | TTA | GAG | AAG | CCA | ATC | TCC | 288 |
| Ala | Ser | Ser | Asp | Thr | Leu | Arg | Asn | Ser | Pro | Leu | Glu | Lys | Pro | Ile | Ser | |
| | | | | 85 | | | | | 90 | | | | | 95 | | |

| AAT | GCT | TTC | TCA | AAA | TCA | CAT | CCA | TAC | AAG | AAA | AGC | AAG | TTC | GAC | TTC | 336 |
| Asn | Ala | Phe | Ser | Lys | Ser | His | Pro | Tyr | Lys | Lys | Ser | Lys | Phe | Asp | Phe | |
| | | | 100 | | | | | 105 | | | | | 110 | | | |

| CTC | AAA | TCT | CGA | AAG | AAA | AAA | GAA | GAG | GAA | GAG | AGA | AAA | AAT | AAA | GAA | 384 |
| Leu | Lys | Ser | Arg | Lys | Lys | Lys | Glu | Glu | Glu | Glu | Arg | Lys | Asn | Lys | Glu | |
| | | 115 | | | | | 120 | | | | | 125 | | | | |

| AAA | GAG | AAG | GAG | GCC | AGT | GTT | CTT | CCT | CCA | GTT | TCG | TTC | TTT | GCC | CTC | 432 |
| Lys | Glu | Lys | Glu | Ala | Ser | Val | Leu | Pro | Pro | Val | Ser | Phe | Phe | Ala | Leu | |
| | 130 | | | | | 135 | | | | | 140 | | | | | |

| TTC | AGG | TTC | GCT | GCA | CCT | CTT | GAG | ATC | ATT | GCC | ATG | GTC | TTG | GGC | CTT | 480 |
| Phe | Arg | Phe | Ala | Ala | Pro | Leu | Glu | Ile | Ile | Ala | Met | Val | Leu | Gly | Leu | |
| 145 | | | | | 150 | | | | | 155 | | | | | 160 | |

| GTG | CTT | GCC | GTT | GCA | GCC | GGA | TCT | TGC | CAA | CCT | TTA | ATG | ACT | TTA | ATA | 528 |
| Val | Leu | Ala | Val | Ala | Ala | Gly | Ser | Cys | Gln | Pro | Leu | Met | Thr | Leu | Ile | |
| | | | | 165 | | | | | 170 | | | | | 175 | | |

| TTC | GGT | CGA | TTA | ACC | ACG | TCT | TTC | ACG | AAT | TAT | GCT | GTC | ATT | GCG | AAC | 576 |
| Phe | Gly | Arg | Leu | Thr | Thr | Ser | Phe | Thr | Asn | Tyr | Ala | Val | Ile | Ala | Asn | |
| | | | 180 | | | | | 185 | | | | | 190 | | | |

| CAA | ATA | TCC | CAA | GGG | GGA | CTT | ACT | CCC | GAG | ACG | TCT | GCG | GCT | TTA | CAA | 624 |
| Gln | Ile | Ser | Gln | Gly | Gly | Leu | Thr | Pro | Glu | Thr | Ser | Ala | Ala | Leu | Gln | |
| | | 195 | | | | | 200 | | | | | 205 | | | | |

| GCA | GCC | AAA | GAT | GAT | CTC | AAG | ACT | CAA | TCT | GGC | CAC | AAT | GCC | CTT | TAT | 672 |
| Ala | Ala | Lys | Asp | Asp | Leu | Lys | Thr | Gln | Ser | Gly | His | Asn | Ala | Leu | Tyr | |
| | 210 | | | | | 215 | | | | | 220 | | | | | |

```
CTG ATG GCC ATT GGC ATT GGA ATG TTT CTA GCG ACT TGG CTT TAC ATG     720
Leu Met Ala Ile Gly Ile Gly Met Phe Leu Ala Thr Trp Leu Tyr Met
225             230                 235                 240

TTC ATC TGG AAT GTT ACT GGC GAG CTC AAC TCT AAA AGG ATT AGA GAG     768
Phe Ile Trp Asn Val Thr Gly Glu Leu Asn Ser Lys Arg Ile Arg Glu
                245                 250                 255

CGT TAC TTG GCT GCA GTG CTT AGA CAG GAG ATT GCC TAC TTT GAT GAT     816
Arg Tyr Leu Ala Ala Val Leu Arg Gln Glu Ile Ala Tyr Phe Asp Asp
                    260                 265                 270

CTG GGC GCC GGA GAA GTC GCC ACT CGC ATT CAG ACC GAT TGT CAC CTT     864
Leu Gly Ala Gly Glu Val Ala Thr Arg Ile Gln Thr Asp Cys His Leu
            275                 280                 285

GTC CAA GAG GGA ACA TCT GAA AAG GTC GCT CTC GTA TTC CAA TAT GCT     912
Val Gln Glu Gly Thr Ser Glu Lys Val Ala Leu Val Phe Gln Tyr Ala
        290                 295                 300

GGT ACT TTT GTC TGC GGT TTT GTT CTA GCT TTT GTC CGG TCA CCT CGT     960
Gly Thr Phe Val Cys Gly Phe Val Leu Ala Phe Val Arg Ser Pro Arg
305                 310                 315                 320

CTT GCG GGC GCT CTT GTT TCC ATC CTG CCA GTC ATC ATG CTC TGC GGC    1008
Leu Ala Gly Ala Leu Val Ser Ile Leu Pro Val Ile Met Leu Cys Gly
                    325                 330                 335

GGT ATT ATG ATG ACG GCC ATG GCC AAA TAT GGG ACT GCG GCT CTT GAT    1056
Gly Ile Met Met Thr Ala Met Ala Lys Tyr Gly Thr Ala Ala Leu Asp
                340                 345                 350

CAC ATC GCG AAA GCG GGC AGC TTG GCA GAA GAG GTC ATA GGA AGT ATC    1104
His Ile Ala Lys Ala Gly Ser Leu Ala Glu Glu Val Ile Gly Ser Ile
            355                 360                 365

AGG ACT GTT CAG GCT TTT GGC AAG GAA AAG ATC TTG GGT GAC AAA TTT    1152
Arg Thr Val Gln Ala Phe Gly Lys Glu Lys Ile Leu Gly Asp Lys Phe
        370                 375                 380

GCC GAT CAC ATT GAG CAG AGC AAG ATT GTC GGT AGA AAA GGC TCC ATC    1200
Ala Asp His Ile Glu Gln Ser Lys Ile Val Gly Arg Lys Gly Ser Ile
385                 390                 395                 400

TTT GAA GGC TTT GGT TTG AGC ATC ATG TTC TTC GTC ATC TAC GCC GCT    1248
Phe Glu Gly Phe Gly Leu Ser Ile Met Phe Phe Val Ile Tyr Ala Ala
                    405                 410                 415

TAT GCC CTC GCC TTC TTC TAC GGT GGC ATT CTC GTC AGT AAC GGC CAA    1296
Tyr Ala Leu Ala Phe Phe Tyr Gly Gly Ile Leu Val Ser Asn Gly Gln
                420                 425                 430

GCC GAC TCC GGT ATC GTC ATC AAC GTT TTC ATG TCC ATC CTC ATT GGT    1344
Ala Asp Ser Gly Ile Val Ile Asn Val Phe Met Ser Ile Leu Ile Gly
            435                 440                 445

TCC TTC TCC ATG GCG ATG CTT GCT CCC GAG TTG GCT GCT GTC ACC AAA    1392
Ser Phe Ser Met Ala Met Leu Ala Pro Glu Leu Ala Ala Val Thr Lys
        450                 455                 460

GCG CGA GGC GCT GCT GCC AAG CTT TTC GCA ACT ATC GAC CGT GTA CCC    1440
Ala Arg Gly Ala Ala Ala Lys Leu Phe Ala Thr Ile Asp Arg Val Pro
465                 470                 475                 480

GCC ATT GAT TCC GCC AGC GAG GAA GGT TTC AAG CCC GAT GGC CTT CGC    1488
Ala Ile Asp Ser Ala Ser Glu Glu Gly Phe Lys Pro Asp Gly Leu Arg
                    485                 490                 495

GGT GAG ATT AGC TTT GAA AAT GTC AAG TTC CAT TAT CCG TCC CGA CCC    1536
Gly Glu Ile Ser Phe Glu Asn Val Lys Phe His Tyr Pro Ser Arg Pro
                500                 505                 510

AGC ATT CCT ATC TTG AAG GGC TTC ACT ACT ACG TTT GAA GCC GGT AAG    1584
Ser Ile Pro Ile Leu Lys Gly Phe Thr Thr Thr Phe Glu Ala Gly Lys
            515                 520                 525

ACT TTC GCT CTC GTC GGA GCT AGT GGA AGC GGA AAG AGT ACT GTC GTT    1632
Thr Phe Ala Leu Val Gly Ala Ser Gly Ser Gly Lys Ser Thr Val Val
        530                 535                 540
```

-continued

| | | | | | | | | | | | | | | | | |
|---|---|---|---|---|---|---|---|---|---|---|---|---|---|---|---|---|
| TCT | CTT | ATT | GAG | AGG | TTT | TAC | GAC | CCC | GTT | AGT | GGT | GTT | GTG | AAG | CTT | 1680 |
| Ser | Leu | Ile | Glu | Arg | Phe | Tyr | Asp | Pro | Val | Ser | Gly | Val | Val | Lys | Leu | |
| 545 | | | | | 550 | | | | | 555 | | | | | 560 | |
| GAC | GGT | AGA | GAT | ATC | AGG | TCG | CTT | AAC | CTC | AAT | TGG | CTT | CGT | CAA | CAG | 1728 |
| Asp | Gly | Arg | Asp | Ile | Arg | Ser | Leu | Asn | Leu | Asn | Trp | Leu | Arg | Gln | Gln | |
| | | | | 565 | | | | | 570 | | | | | 575 | | |
| ATT | GGT | CTT | GTA | TCT | CAG | GAA | CCC | ACT | CTT | TTC | GGT | ACC | ACC | GTC | CGC | 1776 |
| Ile | Gly | Leu | Val | Ser | Gln | Glu | Pro | Thr | Leu | Phe | Gly | Thr | Thr | Val | Arg | |
| | | | 580 | | | | | 585 | | | | | 590 | | | |
| GGT | AAC | GTC | GAA | CAC | GGT | CTC | ATC | GGC | TCC | AGA | TAT | GAG | AAT | GCC | TCT | 1824 |
| Gly | Asn | Val | Glu | His | Gly | Leu | Ile | Gly | Ser | Arg | Tyr | Glu | Asn | Ala | Ser | |
| | | 595 | | | | | 600 | | | | | 605 | | | | |
| CTC | GAG | GAA | AAA | TTT | GAG | CTT | GTG | AAG | AAG | GCT | TGT | GTC | GAT | GCC | AAC | 1872 |
| Leu | Glu | Glu | Lys | Phe | Glu | Leu | Val | Lys | Lys | Ala | Cys | Val | Asp | Ala | Asn | |
| | 610 | | | | | 615 | | | | | 620 | | | | | |
| GCC | CAT | AAT | TTT | ATC | ATG | AAA | CTT | CCG | CAA | GGT | TAT | GAT | ACC | ATG | GTT | 1920 |
| Ala | His | Asn | Phe | Ile | Met | Lys | Leu | Pro | Gln | Gly | Tyr | Asp | Thr | Met | Val | |
| 625 | | | | | 630 | | | | | 635 | | | | | 640 | |
| GGT | GAG | CGC | GGT | ATG | CTG | TTA | TCT | GGT | GGT | CAG | AAG | CAG | CGA | GTT | GCG | 1968 |
| Gly | Glu | Arg | Gly | Met | Leu | Leu | Ser | Gly | Gly | Gln | Lys | Gln | Arg | Val | Ala | |
| | | | | 645 | | | | | 650 | | | | | 655 | | |
| ATT | GCT | CGT | GCT | ATC | GTT | TCC | GAC | CCT | AGG | ATT | TTG | TTG | TTG | GAC | GAA | 2016 |
| Ile | Ala | Arg | Ala | Ile | Val | Ser | Asp | Pro | Arg | Ile | Leu | Leu | Leu | Asp | Glu | |
| | | | 660 | | | | | 665 | | | | | 670 | | | |
| GCT | ACC | TCT | GCT | CTT | GAC | ACT | CAG | AGC | GAA | GGT | ATT | GTG | CAA | GAT | GCT | 2064 |
| Ala | Thr | Ser | Ala | Leu | Asp | Thr | Gln | Ser | Glu | Gly | Ile | Val | Gln | Asp | Ala | |
| | | 675 | | | | | 680 | | | | | 685 | | | | |
| TTG | GAC | AAG | GCC | TCG | CGA | GGC | AGG | ACT | ACT | ATC | ACC | ATT | GCT | CAT | AGG | 2112 |
| Leu | Asp | Lys | Ala | Ser | Arg | Gly | Arg | Thr | Thr | Ile | Thr | Ile | Ala | His | Arg | |
| | 690 | | | | | 695 | | | | | 700 | | | | | |
| TTA | TCT | ACC | ATT | CGA | GAT | GCC | GAC | AGA | ATT | TAC | GTG | ATG | GGT | GGT | GGC | 2160 |
| Leu | Ser | Thr | Ile | Arg | Asp | Ala | Asp | Arg | Ile | Tyr | Val | Met | Gly | Gly | Gly | |
| 705 | | | | | 710 | | | | | 715 | | | | | 720 | |
| GAA | GTA | CTG | GAG | CAG | GGT | TCT | CAC | AAC | GAT | CTT | CTC | GCC | AAC | GAA | AAC | 2208 |
| Glu | Val | Leu | Glu | Gln | Gly | Ser | His | Asn | Asp | Leu | Leu | Ala | Asn | Glu | Asn | |
| | | | | 725 | | | | | 730 | | | | | 735 | | |
| GGT | CCT | TAC | GCA | CAA | CTT | GTC | AAC | AAT | CAA | AAA | CTT | GCT | CAA | GAA | GCT | 2256 |
| Gly | Pro | Tyr | Ala | Gln | Leu | Val | Asn | Asn | Gln | Lys | Leu | Ala | Gln | Glu | Ala | |
| | | | 740 | | | | | 745 | | | | | 750 | | | |
| GCT | GCT | GAA | GCC | CTC | CAG | GTG | GAT | GAC | GAT | ATC | GAG | GAC | CCT | GAC | GAT | 2304 |
| Ala | Ala | Glu | Ala | Leu | Gln | Val | Asp | Asp | Asp | Ile | Glu | Asp | Pro | Asp | Asp | |
| | | 755 | | | | | 760 | | | | | 765 | | | | |
| GCC | GTT | TTC | ATT | GGC | GGT | TCT | TCG | CCT | ATG | CAA | GAA | AAA | GAC | AAA | CAG | 2352 |
| Ala | Val | Phe | Ile | Gly | Gly | Ser | Ser | Pro | Met | Gln | Glu | Lys | Asp | Lys | Gln | |
| | 770 | | | | | 775 | | | | | 780 | | | | | |
| CTT | CAT | CGC | GCA | GTG | ACT | GGA | AGG | TCT | TTG | GCC | AGT | ATC | GCC | ATG | GAC | 2400 |
| Leu | His | Arg | Ala | Val | Thr | Gly | Arg | Ser | Leu | Ala | Ser | Ile | Ala | Met | Asp | |
| 785 | | | | | 790 | | | | | 795 | | | | | 800 | |
| GAC | ATC | CAA | GCC | AAG | AGG | GCG | GAG | GAA | GTC | GCA | GGT | GAG | GAC | AAG | ATA | 2448 |
| Asp | Ile | Gln | Ala | Lys | Arg | Ala | Glu | Glu | Val | Ala | Gly | Glu | Asp | Lys | Ile | |
| | | | | 805 | | | | | 810 | | | | | 815 | | |
| CCT | TCA | AGC | TTT | GGT | CTG | TAT | GCC | AGG | CTG | TTG | AGG | ATG | AAT | TCC | GCC | 2496 |
| Pro | Ser | Ser | Phe | Gly | Leu | Tyr | Ala | Arg | Leu | Leu | Arg | Met | Asn | Ser | Ala | |
| | | | 820 | | | | | 825 | | | | | 830 | | | |
| GAT | AAA | TTT | ATA | TAC | ATC | ATA | GCG | TTT | ATC | GCC | GCC | ATC | TGC | GCA | GGC | 2544 |
| Asp | Lys | Phe | Ile | Tyr | Ile | Ile | Ala | Phe | Ile | Ala | Ala | Ile | Cys | Ala | Gly | |
| | | 835 | | | | | 840 | | | | | 845 | | | | |
| ATG | GTT | TAT | CCT | TCT | TTG | GCC | ATC | CTC | TTT | GGC | AAA | GCC | CTC | TCC | GAC | 2592 |
| Met | Val | Tyr | Pro | Ser | Leu | Ala | Ile | Leu | Phe | Gly | Lys | Ala | Leu | Ser | Asp | |
| | 850 | | | | | 855 | | | | | 860 | | | | | |

| | | | | | | | | | | | | | | | | |
|---|---|---|---|---|---|---|---|---|---|---|---|---|---|---|---|---|
| TTT | GAG | ATT | CAA | GAT | CCT | GCC | GAA | CTT | CGA | CAT | GCT | CTC | AGT | CGC | AGT | 2640 |
| Phe | Glu | Ile | Gln | Asp | Pro | Ala | Glu | Leu | Arg | His | Ala | Leu | Ser | Arg | Ser | |
| 865 | | | | | 870 | | | | | 875 | | | | | 880 | |
| GCC | CTG | TGG | TAC | TTT | ATC | ACT | GCT | CTT | GCG | GCT | GCA | TTT | GTC | ATC | TTC | 2688 |
| Ala | Leu | Trp | Tyr | Phe | Ile | Thr | Ala | Leu | Ala | Ala | Ala | Phe | Val | Ile | Phe | |
| | | | | 885 | | | | | 890 | | | | | 895 | | |
| TTC | CAA | AGT | GCC | GGC | TTC | TCT | CGC | GCC | GGT | TGG | GAT | TTG | AAC | GGT | GTC | 2736 |
| Phe | Gln | Ser | Ala | Gly | Phe | Ser | Arg | Ala | Gly | Trp | Asp | Leu | Asn | Gly | Val | |
| | | 900 | | | | | 905 | | | | | 910 | | | | |
| TTG | AGA | AAA | AAG | TTG | TTC | ACT | GCT | ACT | TTG | CGA | CAT | GAC | ATC | GAA | TGG | 2784 |
| Leu | Arg | Lys | Lys | Leu | Phe | Thr | Ala | Thr | Leu | Arg | His | Asp | Ile | Glu | Trp | |
| | | 915 | | | | | 920 | | | | | 925 | | | | |
| TTC | GAC | GAG | GAA | CGC | AAC | TCT | ACT | GGT | GCC | GTC | ACA | TCC | AAC | CTT | GCC | 2832 |
| Phe | Asp | Glu | Glu | Arg | Asn | Ser | Thr | Gly | Ala | Val | Thr | Ser | Asn | Leu | Ala | |
| | 930 | | | | | 935 | | | | | 940 | | | | | |
| GAT | CAA | CCT | CAG | AAG | GTG | CAA | GGT | CTG | TTT | GGG | CCT | ACT | TTG | GGT | ACA | 2880 |
| Asp | Gln | Pro | Gln | Lys | Val | Gln | Gly | Leu | Phe | Gly | Pro | Thr | Leu | Gly | Thr | |
| 945 | | | | | 950 | | | | | 955 | | | | | 960 | |
| GTC | GTC | CAG | TCC | TGC | GCC | ACT | CTC | ATC | GGT | GGT | TGT | ATT | ATC | GGC | TTG | 2928 |
| Val | Val | Gln | Ser | Cys | Ala | Thr | Leu | Ile | Gly | Gly | Cys | Ile | Ile | Gly | Leu | |
| | | | | 965 | | | | | 970 | | | | | 975 | | |
| TGC | TAC | GGT | CCT | CTT | CTC | GCT | CTG | ATC | GGT | ATC | GCT | TGT | ATC | CCC | ATC | 2976 |
| Cys | Tyr | Gly | Pro | Leu | Leu | Ala | Leu | Ile | Gly | Ile | Ala | Cys | Ile | Pro | Ile | |
| | | | 980 | | | | | 985 | | | | | 990 | | | |
| CTT | GTC | TCT | GGA | GGT | TAT | ATT | CGT | CTC | AAG | GTC | GTT | GTA | CTC | AAG | GAC | 3024 |
| Leu | Val | Ser | Gly | Gly | Tyr | Ile | Arg | Leu | Lys | Val | Val | Val | Leu | Lys | Asp | |
| | | 995 | | | | | 1000 | | | | | 1005 | | | | |
| CAA | CGT | ATG | AAG | AAG | CTC | CAT | GCC | GCT | AGT | GCA | CAT | CTT | GCC | AGT | GAA | 3072 |
| Gln | Arg | Met | Lys | Lys | Leu | His | Ala | Ala | Ser | Ala | His | Leu | Ala | Ser | Glu | |
| | 1010 | | | | | 1015 | | | | | 1020 | | | | | |
| GCT | GCT | GGA | GCC | GTT | AAG | ACA | GTA | GCC | AGT | CTT | ACC | AGG | GAG | AAG | GAT | 3120 |
| Ala | Ala | Gly | Ala | Val | Lys | Thr | Val | Ala | Ser | Leu | Thr | Arg | Glu | Lys | Asp | |
| 1025 | | | | | 1030 | | | | | 1035 | | | | | 1040 | |
| GTA | AGG | AGA | ATC | TAT | TCT | GAA | GCT | CTT | AAA | GCT | CCT | ATG | AAA | TTA | AAT | 3168 |
| Val | Arg | Arg | Ile | Tyr | Ser | Glu | Ala | Leu | Lys | Ala | Pro | Met | Lys | Leu | Asn | |
| | | | | 1045 | | | | | 1050 | | | | | 1055 | | |
| TTC | CGT | ACT | TCT | ATT | AAA | TCC | CAG | TGT | CTC | TTT | GCG | GCG | AGT | CAG | GGT | 3216 |
| Phe | Arg | Thr | Ser | Ile | Lys | Ser | Gln | Cys | Leu | Phe | Ala | Ala | Ser | Gln | Gly | |
| | | | | 1060 | | | | | 1065 | | | | | 1070 | | |
| TTG | ACT | TTC | TGT | ATC | ATT | GCT | CTG | GTC | TTC | TAC | ATT | GGC | GCA | TTA | TGG | 3264 |
| Leu | Thr | Phe | Cys | Ile | Ile | Ala | Leu | Val | Phe | Tyr | Ile | Gly | Ala | Leu | Trp | |
| | | 1075 | | | | | 1080 | | | | | 1085 | | | | |
| ATC | ATC | GAT | GCC | AAA | TAC | TCC | ACT | GCT | AGT | TTC | TAT | ACT | GTC | TTG | AAC | 3312 |
| Ile | Ile | Asp | Ala | Lys | Tyr | Ser | Thr | Ala | Ser | Phe | Tyr | Thr | Val | Leu | Asn | |
| | | 1090 | | | | | 1095 | | | | | 1100 | | | | |
| TCC | ATT | GTC | TTT | GCG | TCT | ATT | CAA | GCT | GGA | AAT | GTC | TTC | ACC | TTC | GTC | 3360 |
| Ser | Ile | Val | Phe | Ala | Ser | Ile | Gln | Ala | Gly | Asn | Val | Phe | Thr | Phe | Val | |
| 1105 | | | | | 1110 | | | | | 1115 | | | | | 1120 | |
| CCG | GAT | GCG | TCC | AAG | GCC | AAT | TCC | TCG | GCC | GCC | TCC | ATC | TTC | CGA | AGC | 3408 |
| Pro | Asp | Ala | Ser | Lys | Ala | Asn | Ser | Ser | Ala | Ala | Ser | Ile | Phe | Arg | Ser | |
| | | | | 1125 | | | | | 1130 | | | | | 1135 | | |
| ATC | GAC | AAT | GAA | CCG | GCT | ATC | AAT | GCT | GAA | TCT | AAT | GAA | GGG | AAG | GTG | 3456 |
| Ile | Asp | Asn | Glu | Pro | Ala | Ile | Asn | Ala | Glu | Ser | Asn | Glu | Gly | Lys | Val | |
| | | | | 1140 | | | | | 1145 | | | | | 1150 | | |
| CTT | GAT | CAC | AAG | CAC | GTC | GTT | GGT | CAT | GTG | CGA | ATT | GAA | GGC | GTT | CAC | 3504 |
| Leu | Asp | His | Lys | His | Val | Val | Gly | His | Val | Arg | Ile | Glu | Gly | Val | His | |
| | | | 1155 | | | | | 1160 | | | | | 1165 | | | |
| TTC | AGG | TAT | CCT | ACC | AGG | CCG | GGA | GTG | AGA | GTA | CTG | AGG | AAT | TTG | ACT | 3552 |
| Phe | Arg | Tyr | Pro | Thr | Arg | Pro | Gly | Val | Arg | Val | Leu | Arg | Asn | Leu | Thr | |
| | | | 1170 | | | | | 1175 | | | | | 1180 | | | |

| | | | | | | | | | | | | | | | | |
|---|---|---|---|---|---|---|---|---|---|---|---|---|---|---|---|---|
|ATT|GAT|GTT|CCT|GCC|GGC|ACT|TAT|GTG|GCA|CTC|GTT|GGT|CCT|TCC|GGT|3600|
|Ile|Asp|Val|Pro|Ala|Gly|Thr|Tyr|Val|Ala|Leu|Val|Gly|Pro|Ser|Gly| |
|1185| | | | |1190| | | | |1195| | | | |1200| |

|TGT|GGA|AAG|TCT|ACC|ACT|ATT|CAA|ATG|CTG|GAG|AGG|TTC|TAC|GAC|CCT|3648|
|Cys|Gly|Lys|Ser|Thr|Thr|Ile|Gln|Met|Leu|Glu|Arg|Phe|Tyr|Asp|Pro|
| | | | |1205| | | | |1210| | | | |1215| |

|TTG|GCT|GGC|CGT|GTG|ACT|TTG|GAT|GGC|ATC|GAT|ATT|AAG|GAG|CTC|AAC|3696|
|Leu|Ala|Gly|Arg|Val|Thr|Leu|Asp|Gly|Ile|Asp|Ile|Lys|Glu|Leu|Asn|
| | | |1220| | | | |1225| | | | |1230| | | |

|TTG|GCG|AGT|TAC|CGT|AGC|CAG|ATC|TCC|CTC|GTT|TCT|CAA|GAA|CCT|ACC|3744|
|Leu|Ala|Ser|Tyr|Arg|Ser|Gln|Ile|Ser|Leu|Val|Ser|Gln|Glu|Pro|Thr|
| | | |1235| | | | |1240| | | | |1245| | | |

|CTT|TAC|GCG|GGT|ACA|ATT|AGG|TTT|AAT|ATT|CTT|TTG|GGC|GCG|AAC|AAG|3792|
|Leu|Tyr|Ala|Gly|Thr|Ile|Arg|Phe|Asn|Ile|Leu|Leu|Gly|Ala|Asn|Lys|
| | |1250| | | | |1255| | | | |1260| | | | |

|CCC|ATA|GAG|GAG|GTG|ACT|CAG|GAT|GAG|ATT|GAT|GCT|GCC|TGC|AAG|GAT|3840|
|Pro|Ile|Glu|Glu|Val|Thr|Gln|Asp|Glu|Ile|Asp|Ala|Ala|Cys|Lys|Asp|
|1265| | | | |1270| | | | |1275| | | | |1280| |

|GCC|AAT|ATT|TAC|GAC|TTT|ATC|GTG|TCC|TTG|CCA|GAT|GGT|TTT|GAC|ACC|3888|
|Ala|Asn|Ile|Tyr|Asp|Phe|Ile|Val|Ser|Leu|Pro|Asp|Gly|Phe|Asp|Thr|
| | | | |1285| | | | |1290| | | | |1295| | |

|GAA|GTG|GGT|GGG|AAA|GGC|TCT|CAG|CTT|TCT|GGT|GGT|CAA|AAG|CAA|CGT|3936|
|Glu|Val|Gly|Gly|Lys|Gly|Ser|Gln|Leu|Ser|Gly|Gly|Gln|Lys|Gln|Arg|
| | | |1300| | | | |1305| | | | |1310| | | |

|ATC|GCT|ATC|GCC|CGT|GCT|CTC|ATT|CGA|AAC|CCT|AAA|GTC|TTG|CTC|CTT|3984|
|Ile|Ala|Ile|Ala|Arg|Ala|Leu|Ile|Arg|Asn|Pro|Lys|Val|Leu|Leu|Leu|
| | |1315| | | | |1320| | | | |1325| | | | |

|GAC|GAA|GCT|ACG|TCC|GCA|CTC|GAC|AGT|CAG|TCA|GAA|AAG|GTC|GTT|CAG|4032|
|Asp|Glu|Ala|Thr|Ser|Ala|Leu|Asp|Ser|Gln|Ser|Glu|Lys|Val|Val|Gln|
| |1330| | | | |1335| | | | |1340| | | | | |

|GAG|GCA|CTT|GAT|AAG|GCA|GCC|AAG|GGT|AGA|ACA|ACC|ATT|GCG|ATT|GCT|4080|
|Glu|Ala|Leu|Asp|Lys|Ala|Ala|Lys|Gly|Arg|Thr|Thr|Ile|Ala|Ile|Ala|
|1345| | | | |1350| | | | |1355| | | | |1360| |

|CAT|CGT|TTG|TCG|TCA|ATT|CAA|CAT|TCT|GAC|CGG|ATT|TAC|TAC|TTC|TCT|4128|
|His|Arg|Leu|Ser|Ser|Ile|Gln|His|Ser|Asp|Arg|Ile|Tyr|Tyr|Phe|Ser|
| | | | |1365| | | | |1370| | | | |1375| | |

|GAA|GGC|AGG|GTA|GCC|GAG|CAT|GGA|ACA|CAT|CAG|GAG|CTT|TTG|GCC|AAG|4176|
|Glu|Gly|Arg|Val|Ala|Glu|His|Gly|Thr|His|Gln|Glu|Leu|Leu|Ala|Lys|
| | | |1380| | | | |1385| | | | |1390| | | |

|AAG|GGT|GGC|TAT|TAT|GAG|CTG|GTT|CAA|ATG|CAA|AAC|CTG|AGT|CGT|CAA|4224|
|Lys|Gly|Gly|Tyr|Tyr|Glu|Leu|Val|Gln|Met|Gln|Asn|Leu|Ser|Arg|Gln|
| | |1395| | | | |1400| | | | |1405| | | | |

( 2 ) INFORMATION FOR SEQ ID NO:2:

( i ) SEQUENCE CHARACTERISTICS:
　　　　( A ) LENGTH: 1408 amino acids
　　　　( B ) TYPE: amino acid
　　　　( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
|Met|Ser|Ala|Ser|Pro|Gly|Leu|Thr|Ala|Ala|Ala|Ala|Gly|Pro|Asp|His|
|1| | | |5| | | | |10| | | | |15| |

|Leu|Gln|Ala|Arg|Arg|Asp|Glu|Lys|Val|Ile|Asp|Ser|Glu|Lys|Asp|Ala|
| | | |20| | | | |25| | | | |30| | |

|Leu|Ala|His|Asp|Ala|His|Ala|Val|Asn|Ser|Gly|Ile|Pro|Tyr|Pro|Thr|
| | |35| | | | |40| | | | |45| | | |

|Ala|Thr|Ala|Pro|Asn|Val|Gly|Ala|Pro|Thr|Val|Pro|Ile|Ser|Val|Gly|
| |50| | | | |55| | | | |60| | | | |

| | | | | | | | | | | | | | | |
|---|---|---|---|---|---|---|---|---|---|---|---|---|---|---|
| Arg | Val | Ser | Ser | Ala | Ala | Glu | Gly | Lys | Ile | Ser | Arg | Ser | Ser | Ile | Ala |
| 65 | | | | | 70 | | | | 75 | | | | | 80 |
| Ala | Ser | Ser | Asp | Thr | Leu | Arg | Asn | Ser | Pro | Leu | Glu | Lys | Pro | Ile | Ser |
| | | | | 85 | | | | | 90 | | | | | 95 | |
| Asn | Ala | Phe | Ser | Lys | Ser | His | Pro | Tyr | Lys | Lys | Ser | Lys | Phe | Asp | Phe |
| | | | 100 | | | | | 105 | | | | | 110 | | |
| Leu | Lys | Ser | Arg | Lys | Lys | Lys | Glu | Glu | Glu | Arg | Lys | Asn | Lys | Glu |
| | | 115 | | | | | 120 | | | | | 125 | | | |
| Lys | Glu | Lys | Glu | Ala | Ser | Val | Leu | Pro | Pro | Val | Ser | Phe | Phe | Ala | Leu |
| | 130 | | | | | 135 | | | | | 140 | | | | |
| Phe | Arg | Phe | Ala | Ala | Pro | Leu | Glu | Ile | Ile | Ala | Met | Val | Leu | Gly | Leu |
| 145 | | | | | 150 | | | | | 155 | | | | | 160 |
| Val | Leu | Ala | Val | Ala | Ala | Gly | Ser | Cys | Gln | Pro | Leu | Met | Thr | Leu | Ile |
| | | | | 165 | | | | | 170 | | | | | 175 | |
| Phe | Gly | Arg | Leu | Thr | Thr | Ser | Phe | Thr | Asn | Tyr | Ala | Val | Ile | Ala | Asn |
| | | | 180 | | | | | 185 | | | | | 190 | | |
| Gln | Ile | Ser | Gln | Gly | Gly | Leu | Thr | Pro | Glu | Thr | Ser | Ala | Ala | Leu | Gln |
| | | | 195 | | | | | 200 | | | | | 205 | | |
| Ala | Ala | Lys | Asp | Asp | Leu | Lys | Thr | Gln | Ser | Gly | His | Asn | Ala | Leu | Tyr |
| | 210 | | | | | 215 | | | | | 220 | | | | |
| Leu | Met | Ala | Ile | Gly | Ile | Gly | Met | Phe | Leu | Ala | Thr | Trp | Leu | Tyr | Met |
| 225 | | | | | 230 | | | | | 235 | | | | | 240 |
| Phe | Ile | Trp | Asn | Val | Thr | Gly | Glu | Leu | Asn | Ser | Lys | Arg | Ile | Arg | Glu |
| | | | | 245 | | | | | 250 | | | | | 255 | |
| Arg | Tyr | Leu | Ala | Ala | Val | Leu | Arg | Gln | Glu | Ile | Ala | Tyr | Phe | Asp | Asp |
| | | | 260 | | | | | 265 | | | | | 270 | | |
| Leu | Gly | Ala | Gly | Glu | Val | Ala | Thr | Arg | Ile | Gln | Thr | Asp | Cys | His | Leu |
| | | | 275 | | | | | 280 | | | | | 285 | | |
| Val | Gln | Glu | Gly | Thr | Ser | Glu | Lys | Val | Ala | Leu | Val | Phe | Gln | Tyr | Ala |
| | 290 | | | | | 295 | | | | | 300 | | | | |
| Gly | Thr | Phe | Val | Cys | Gly | Phe | Val | Leu | Ala | Phe | Val | Arg | Ser | Pro | Arg |
| 305 | | | | | 310 | | | | | 315 | | | | | 320 |
| Leu | Ala | Gly | Ala | Leu | Val | Ser | Ile | Leu | Pro | Val | Ile | Met | Leu | Cys | Gly |
| | | | | 325 | | | | | 330 | | | | | 335 | |
| Gly | Ile | Met | Met | Thr | Ala | Met | Ala | Lys | Tyr | Gly | Thr | Ala | Ala | Leu | Asp |
| | | | 340 | | | | | 345 | | | | | 350 | | |
| His | Ile | Ala | Lys | Ala | Gly | Ser | Leu | Ala | Glu | Glu | Val | Ile | Gly | Ser | Ile |
| | | 355 | | | | | 360 | | | | | 365 | | | |
| Arg | Thr | Val | Gln | Ala | Phe | Gly | Lys | Glu | Lys | Ile | Leu | Gly | Asp | Lys | Phe |
| | 370 | | | | | 375 | | | | | 380 | | | | |
| Ala | Asp | His | Ile | Glu | Gln | Ser | Lys | Ile | Val | Gly | Arg | Lys | Gly | Ser | Ile |
| 385 | | | | | 390 | | | | | 395 | | | | | 400 |
| Phe | Glu | Gly | Phe | Gly | Leu | Ser | Ile | Met | Phe | Phe | Val | Ile | Tyr | Ala | Ala |
| | | | | 405 | | | | | 410 | | | | | 415 | |
| Tyr | Ala | Leu | Ala | Phe | Phe | Tyr | Gly | Gly | Ile | Leu | Val | Ser | Asn | Gly | Gln |
| | | | 420 | | | | | 425 | | | | | 430 | | |
| Ala | Asp | Ser | Gly | Ile | Val | Ile | Asn | Val | Phe | Met | Ser | Ile | Leu | Ile | Gly |
| | | 435 | | | | | 440 | | | | | 445 | | | |
| Ser | Phe | Ser | Met | Ala | Met | Leu | Ala | Pro | Glu | Leu | Ala | Ala | Val | Thr | Lys |
| | 450 | | | | | 455 | | | | | 460 | | | | |
| Ala | Arg | Gly | Ala | Ala | Ala | Lys | Leu | Phe | Ala | Thr | Ile | Asp | Arg | Val | Pro |
| 465 | | | | | 470 | | | | | 475 | | | | | 480 |
| Ala | Ile | Asp | Ser | Ala | Ser | Glu | Glu | Gly | Phe | Lys | Pro | Asp | Gly | Leu | Arg |

-continued

|     |     |     |     | 485 |     |     |     | 490 |     |     |     | 495 |     |
|---|---|---|---|---|---|---|---|---|---|---|---|---|---|
| Gly | Glu | Ile | Ser | Phe | Glu | Asn | Val | Lys | Phe | His | Tyr | Pro | Ser | Arg | Pro |
|     |     |     | 500 |     |     |     |     | 505 |     |     |     | 510 |     |
| Ser | Ile | Pro | Ile | Leu | Lys | Gly | Phe | Thr | Thr | Thr | Phe | Glu | Ala | Gly | Lys |
|     |     |     | 515 |     |     |     |     | 520 |     |     |     | 525 |     |
| Thr | Phe | Ala | Leu | Val | Gly | Ala | Ser | Gly | Ser | Gly | Lys | Ser | Thr | Val | Val |
|     |     |     | 530 |     |     |     |     | 535 |     |     |     | 540 |     |
| Ser | Leu | Ile | Glu | Arg | Phe | Tyr | Asp | Pro | Val | Ser | Gly | Val | Val | Lys | Leu |
| 545 |     |     |     |     |     | 550 |     |     |     |     | 555 |     |     |     | 560 |
| Asp | Gly | Arg | Asp | Ile | Arg | Ser | Leu | Asn | Leu | Asn | Trp | Leu | Arg | Gln | Gln |
|     |     |     |     | 565 |     |     |     | 570 |     |     |     |     | 575 |     |
| Ile | Gly | Leu | Val | Ser | Gln | Glu | Pro | Thr | Leu | Phe | Gly | Thr | Thr | Val | Arg |
|     |     |     | 580 |     |     |     |     | 585 |     |     |     | 590 |     |
| Gly | Asn | Val | Glu | His | Gly | Leu | Ile | Gly | Ser | Arg | Tyr | Glu | Asn | Ala | Ser |
|     |     |     | 595 |     |     |     |     | 600 |     |     |     | 605 |     |
| Leu | Glu | Glu | Lys | Phe | Glu | Leu | Val | Lys | Lys | Ala | Cys | Val | Asp | Ala | Asn |
|     |     |     | 610 |     |     |     |     | 615 |     |     |     | 620 |     |
| Ala | His | Asn | Phe | Ile | Met | Lys | Leu | Pro | Gln | Gly | Tyr | Asp | Thr | Met | Val |
| 625 |     |     |     |     |     | 630 |     |     |     |     | 635 |     |     |     | 640 |
| Gly | Glu | Arg | Gly | Met | Leu | Leu | Ser | Gly | Gly | Gln | Lys | Gln | Arg | Val | Ala |
|     |     |     |     | 645 |     |     |     |     | 650 |     |     |     | 655 |     |
| Ile | Ala | Arg | Ala | Ile | Val | Ser | Asp | Pro | Arg | Ile | Leu | Leu | Leu | Asp | Glu |
|     |     |     | 660 |     |     |     |     | 665 |     |     |     | 670 |     |
| Ala | Thr | Ser | Ala | Leu | Asp | Thr | Gln | Ser | Glu | Gly | Ile | Val | Gln | Asp | Ala |
|     |     |     | 675 |     |     |     |     | 680 |     |     |     | 685 |     |
| Leu | Asp | Lys | Ala | Ser | Arg | Gly | Arg | Thr | Thr | Ile | Thr | Ile | Ala | His | Arg |
|     | 690 |     |     |     |     | 695 |     |     |     |     | 700 |     |     |     |
| Leu | Ser | Thr | Ile | Arg | Asp | Ala | Asp | Arg | Ile | Tyr | Val | Met | Gly | Gly | Gly |
| 705 |     |     |     | 710 |     |     |     |     | 715 |     |     |     |     | 720 |
| Glu | Val | Leu | Glu | Gln | Gly | Ser | His | Asn | Asp | Leu | Leu | Ala | Asn | Glu | Asn |
|     |     |     |     | 725 |     |     |     | 730 |     |     |     |     | 735 |     |
| Gly | Pro | Tyr | Ala | Gln | Leu | Val | Asn | Asn | Gln | Lys | Leu | Ala | Gln | Glu | Ala |
|     |     |     | 740 |     |     |     |     | 745 |     |     |     | 750 |     |
| Ala | Ala | Glu | Ala | Leu | Gln | Val | Asp | Asp | Ile | Glu | Asp | Pro | Asp | Asp |
|     |     |     | 755 |     |     |     | 760 |     |     |     | 765 |     |     |
| Ala | Val | Phe | Ile | Gly | Gly | Ser | Ser | Pro | Met | Gln | Glu | Lys | Asp | Lys | Gln |
|     |     |     | 770 |     |     | 775 |     |     |     |     | 780 |     |     |     |
| Leu | His | Arg | Ala | Val | Thr | Gly | Arg | Ser | Leu | Ala | Ser | Ile | Ala | Met | Asp |
| 785 |     |     |     |     | 790 |     |     |     | 795 |     |     |     |     | 800 |
| Asp | Ile | Gln | Ala | Lys | Arg | Ala | Glu | Val | Ala | Gly | Glu | Asp | Lys | Ile |
|     |     |     |     | 805 |     |     |     |     | 810 |     |     |     | 815 |
| Pro | Ser | Ser | Phe | Gly | Leu | Tyr | Ala | Arg | Leu | Leu | Arg | Met | Asn | Ser | Ala |
|     |     |     | 820 |     |     |     |     | 825 |     |     |     | 830 |     |
| Asp | Lys | Phe | Ile | Tyr | Ile | Ile | Ala | Phe | Ile | Ala | Ala | Ile | Cys | Ala | Gly |
|     |     | 835 |     |     |     |     | 840 |     |     |     |     | 845 |     |
| Met | Val | Tyr | Pro | Ser | Leu | Ala | Ile | Leu | Phe | Gly | Lys | Ala | Leu | Ser | Asp |
|     | 850 |     |     |     | 855 |     |     |     |     | 860 |     |     |     |     |
| Phe | Glu | Ile | Gln | Asp | Pro | Ala | Glu | Leu | Arg | His | Ala | Leu | Ser | Arg | Ser |
| 865 |     |     |     |     | 870 |     |     |     | 875 |     |     |     |     | 880 |
| Ala | Leu | Trp | Tyr | Phe | Ile | Thr | Ala | Leu | Ala | Ala | Ala | Phe | Val | Ile | Phe |
|     |     |     |     | 885 |     |     |     | 890 |     |     |     |     | 895 |
| Phe | Gln | Ser | Ala | Gly | Phe | Ser | Arg | Ala | Gly | Trp | Asp | Leu | Asn | Gly | Val |
|     |     |     | 900 |     |     |     | 905 |     |     |     |     | 910 |     |

```
Leu  Arg  Lys  Lys  Leu  Phe  Thr  Ala  Thr  Leu  Arg  His  Asp  Ile  Glu  Trp
          915                      920                     925

Phe  Asp  Glu  Glu  Arg  Asn  Ser  Thr  Gly  Ala  Val  Thr  Ser  Asn  Leu  Ala
     930                      935                     940

Asp  Gln  Pro  Gln  Lys  Val  Gln  Gly  Leu  Phe  Gly  Pro  Thr  Leu  Gly  Thr
945                      950                     955                          960

Val  Val  Gln  Ser  Cys  Ala  Thr  Leu  Ile  Gly  Gly  Cys  Ile  Ile  Gly  Leu
               965                     970                          975

Cys  Tyr  Gly  Pro  Leu  Leu  Ala  Leu  Ile  Gly  Ile  Ala  Cys  Ile  Pro  Ile
               980                     985                     990

Leu  Val  Ser  Gly  Gly  Tyr  Ile  Arg  Leu  Lys  Val  Val  Leu  Lys  Asp
          995                     1000                    1005

Gln  Arg  Met  Lys  Lys  Leu  His  Ala  Ala  Ser  Ala  His  Leu  Ala  Ser  Glu
          1010                    1015                    1020

Ala  Ala  Gly  Ala  Val  Lys  Thr  Val  Ala  Ser  Leu  Thr  Arg  Glu  Lys  Asp
1025                     1030                    1035                         1040

Val  Arg  Arg  Ile  Tyr  Ser  Glu  Ala  Leu  Lys  Ala  Pro  Met  Lys  Leu  Asn
                    1045                    1050                    1055

Phe  Arg  Thr  Ser  Ile  Lys  Ser  Gln  Cys  Leu  Phe  Ala  Ala  Ser  Gln  Gly
               1060                    1065                    1070

Leu  Thr  Phe  Cys  Ile  Ile  Ala  Leu  Val  Phe  Tyr  Ile  Gly  Ala  Leu  Trp
          1075                    1080                    1085

Ile  Ile  Asp  Ala  Lys  Tyr  Ser  Thr  Ala  Ser  Phe  Tyr  Thr  Val  Leu  Asn
     1090                     1095                    1100

Ser  Ile  Val  Phe  Ala  Ser  Ile  Gln  Ala  Gly  Asn  Val  Phe  Thr  Phe  Val
1105                     1110                    1115                         1120

Pro  Asp  Ala  Ser  Lys  Ala  Asn  Ser  Ser  Ala  Ala  Ser  Ile  Phe  Arg  Ser
                    1125                    1130                    1135

Ile  Asp  Asn  Glu  Pro  Ala  Ile  Asn  Ala  Glu  Ser  Asn  Glu  Gly  Lys  Val
                    1140                    1145                    1150

Leu  Asp  His  Lys  His  Val  Val  Gly  His  Val  Arg  Ile  Glu  Gly  Val  His
                    1155                    1160                    1165

Phe  Arg  Tyr  Pro  Thr  Arg  Pro  Gly  Val  Arg  Val  Leu  Arg  Asn  Leu  Thr
     1170                     1175                    1180

Ile  Asp  Val  Pro  Ala  Gly  Thr  Tyr  Val  Ala  Leu  Val  Gly  Pro  Ser  Gly
1185                     1190                    1195                         1200

Cys  Gly  Lys  Ser  Thr  Thr  Ile  Gln  Met  Leu  Glu  Arg  Phe  Tyr  Asp  Pro
               1205                    1210                    1215

Leu  Ala  Gly  Arg  Val  Thr  Leu  Asp  Gly  Ile  Asp  Ile  Lys  Glu  Leu  Asn
               1220                    1225                    1230

Leu  Ala  Ser  Tyr  Arg  Ser  Gln  Ile  Ser  Leu  Val  Ser  Gln  Glu  Pro  Thr
               1235                    1240                    1245

Leu  Tyr  Ala  Gly  Thr  Ile  Arg  Phe  Asn  Ile  Leu  Leu  Gly  Ala  Asn  Lys
     1250                     1255                    1260

Pro  Ile  Glu  Glu  Val  Thr  Gln  Asp  Glu  Ile  Asp  Ala  Ala  Cys  Lys  Asp
1265                     1270                    1275                         1280

Ala  Asn  Ile  Tyr  Asp  Phe  Ile  Val  Ser  Leu  Pro  Asp  Gly  Phe  Asp  Thr
               1285                    1290                    1295

Glu  Val  Gly  Gly  Lys  Gly  Ser  Gln  Leu  Ser  Gly  Gly  Gln  Lys  Gln  Arg
               1300                    1305                    1310

Ile  Ala  Ile  Ala  Arg  Ala  Leu  Ile  Arg  Asn  Pro  Lys  Val  Leu  Leu  Leu
               1315                    1320                    1325

Asp  Glu  Ala  Thr  Ser  Ala  Leu  Asp  Ser  Gln  Ser  Glu  Lys  Val  Val  Gln
     1330                     1335                    1340
```

| Glu | Ala | Leu | Asp | Lys | Ala | Ala | Lys | Gly | Arg | Thr | Thr | Ile | Ala | Ile | Ala |
| 1345 | | | | 1350 | | | | | 1355 | | | | | | 1360 |

| His | Arg | Leu | Ser | Ser | Ile | Gln | His | Ser | Asp | Arg | Ile | Tyr | Tyr | Phe | Ser |
| | | | | 1365 | | | | | 1370 | | | | | 1375 | |

| Glu | Gly | Arg | Val | Ala | Glu | His | Gly | Thr | His | Gln | Glu | Leu | Leu | Ala | Lys |
| | | | 1380 | | | | | 1385 | | | | | 1390 | | |

| Lys | Gly | Gly | Tyr | Tyr | Glu | Leu | Val | Gln | Met | Gln | Asn | Leu | Ser | Arg | Gln |
| | 1395 | | | | | | 1400 | | | | | 1405 | | | |

( 2 ) INFORMATION FOR SEQ ID NO:3:

( i ) SEQUENCE CHARACTERISTICS:
        ( A ) LENGTH: 6143 base pairs
        ( B ) TYPE: nucleic acid
        ( C ) STRANDEDNESS: double
        ( D ) TOPOLOGY: linear     ( i x ) FEATURE:
        ( A ) NAME/KEY: exon
        ( B ) LOCATION: 541..1072

( i x ) FEATURE:
        ( A ) NAME/KEY: exon
        ( B ) LOCATION: 1130..1395

( i x ) FEATURE:
        ( A ) NAME/KEY: exon
        ( B ) LOCATION: 1443..1872

( i x ) FEATURE:
        ( A ) NAME/KEY: exon
        ( B ) LOCATION: 1925..2428

( i x ) FEATURE:
        ( A ) NAME/KEY: exon
        ( B ) LOCATION: 2479..2863

( i x ) FEATURE:
        ( A ) NAME/KEY: exon
        ( B ) LOCATION: 2913..3009

( i x ) FEATURE:
        ( A ) NAME/KEY: exon
        ( B ) LOCATION: 3076..3379

( i x ) FEATURE:
        ( A ) NAME/KEY: exon
        ( B ) LOCATION: 3438..3561

( i x ) FEATURE:
        ( A ) NAME/KEY: exon
        ( B ) LOCATION: 3614..3776

( i x ) FEATURE:
        ( A ) NAME/KEY: exon
        ( B ) LOCATION: 3831..3966

( i x ) FEATURE:
        ( A ) NAME/KEY: exon
        ( B ) LOCATION: 4016..4244

( i x ) FEATURE:
        ( A ) NAME/KEY: exon
        ( B ) LOCATION: 4291..4438

( i x ) FEATURE:
        ( A ) NAME/KEY: exon
        ( B ) LOCATION: 4487..4743

( i x ) FEATURE:
        ( A ) NAME/KEY: exon
        ( B ) LOCATION: 4793..4958

( i x ) FEATURE:
        ( A ) NAME/KEY: exon (B) LOCATION: 5006..5113

(ix) FEATURE:
 (A) NAME/KEY: exon
 (B) LOCATION: 5162..5500

(ix) FEATURE:
 (A) NAME/KEY: exon
 (B) LOCATION: 5553..5588

(xi) SEQUENCE DESCRIPTION: SEQ ID NO:3:

| | | | | | |
|---|---|---|---|---|---|
| GTACTCCCTG | CTGCATGATG | CTCCTTGCGG | GCTCGCGGTT | CCCTGCCCGG | CTGTCCTTTT | 60 |
| CCTTTAAATT | TGTTTTCGGA | ATCTTAAGCA | CGCTGTCGCC | AGCCCGGCGG | CCGCTTGTCC | 120 |
| ATCGGCAGAT | CGGGCGCCGT | ACTTTTGCC | GTATATGAAT | ACGAGTGGCG | TTTTGATACA | 180 |
| CCGTCCGTCC | CTCTCTTCCT | TCCTTTTTGC | TACTGTACAT | CCGCCCCTTG | TGCCACCATT | 240 |
| TCCCGAAAAA | CACAAGCAGA | AGAGATAAAA | TCGGTGAGTG | AAAAGAGAAA | GTAAGGCTCC | 300 |
| TCGGTGCAGA | CACATGCTCA | CAGTTTCCGT | CAGCCGCCAG | CCGAGGTCGC | CGCGTCACTA | 360 |
| CTCCATCCCG | GGCATTTTCT | GGCCAAAAAC | AAACCACCAA | CCGTTGACAT | TGCATTTCGC | 420 |
| AGCTCTTACA | CAACTCCATC | TCTTCCTTTC | CTATCAACAC | ACTGAATTTG | ATACAACATA | 480 |
| CCTGCAAAGT | ACACCCCACT | CAATTGGTAA | ATTCACCTAC | CCATTACCGA | AGCGCTACGA | 540 |
| ATGTCTGCTT | CTCCAGGACT | CACTGCGGCT | GCAGCCGGCC | CCGACCATCT | TCAAGCCCGC | 600 |
| CGTGACGAAA | AAGTCATCGA | CTCCGAGAAG | GATGCTCTTG | CCCACGATGC | TCATGCTGTG | 660 |
| AACTCTGGTA | TACCTTACCC | AACAGCCACT | GCACCTAATG | TCGGAGCACC | CACTGTCCCA | 720 |
| ATCAGCGTTG | GTCGCGTTTC | GTCGGCAGCC | GAAGGAAAGA | TTAGCCGCTC | CTCTATCGCC | 780 |
| GCTTCCTCTG | ACACTCTCCG | CAACTCTCCG | TTAGAGAAGC | CAATCTCCAA | TGCTTTCTCA | 840 |
| AAATCACATC | CATACAAGAA | AAGCAAGTTC | GACTTCCTCA | AATCTCGAAA | GAAAAAAGAA | 900 |
| GAGGAAGAGA | GAAAAAATAA | AGAAAAAGAG | AAGGAGGCCA | GTGTTCTTCC | TCCAGTTTCG | 960 |
| TTCTTTGCCC | TCTTCAGGTT | CGCTGCACCT | CTTGAGATCA | TTGCCATGGT | CTTGGGCCTT | 1020 |
| GTGCTTGCCG | TTGCAGCCGG | ATCTTGCCAA | CCTTTAATGA | CTTTAATATT | CGGTAAAAAA | 1080 |
| TCAAGCCTCT | CTCGCTAGGT | TTGTAGTGGC | TGACGTGATC | AATTTGCAGG | TCGATTAACC | 1140 |
| ACGTCTTTCA | CGAATTATGC | TGTCATTGCG | AACCAAATAT | CCCAAGGGGG | ACTTACTCCC | 1200 |
| GAGACGTCTG | CGGCTTTACA | AGCAGCCAAA | GATGATCTCA | AGACTCAATC | TGGCCACAAT | 1260 |
| GCCCTTTATC | TGATGGCCAT | TGGCATTGGA | ATGTTTCTAG | CGACTTGGCT | TTACATGTTC | 1320 |
| ATCTGGAATG | TTACTGGCGA | GCTCAACTCT | AAAAGGATTA | GAGAGCGTTA | CTTGGCTGCA | 1380 |
| GTGCTTAGAC | AGGAGGTAAG | CTTGTTCTCA | AATCAAGTGA | GACGAGCTTG | ACGTGAATGT | 1440 |
| AGATTGCCTA | CTTTGATGAT | CTGGGCGCCG | GAGAAGTCGC | CACTCGCATT | CAGACCGATT | 1500 |
| GTCACCTTGT | CCAAGAGGGA | ACATCTGAAA | AGGTCGCTCT | CGTATTCCAA | TATGCTGGTA | 1560 |
| CTTTTGTCTG | CGGTTTTGTT | CTAGCTTTTG | TCCGGTCACC | TCGTCTTGCG | GGCGCTCTTG | 1620 |
| TTTCCATCCT | GCCAGTCATC | ATGCTCTGCG | GCGGTATTAT | GATGACGGCC | ATGGCCAAAT | 1680 |
| ATGGGACTGC | GGCTCTTGAT | CACATCGCGA | AAGCGGGCAG | CTTGGCAGAA | GAGGTCATAG | 1740 |
| GAAGTATCAG | GACTGTTCAG | GCTTTTGGCA | AGGAAAAGAT | CTTGGGTGAC | AAATTTGCCG | 1800 |
| ATCACATTGA | GCAGAGCAAG | ATTGTCGGTA | GAAAAGGCTC | CATCTTTGAA | GGCTTTGGTT | 1860 |
| TGAGCATCAT | GTGTAAGCGC | CGTTCACCTC | TACATCCCTA | CATTTTCGCT | TATGATAATT | 1920 |
| ACAGTCTTCG | TCATCTACGC | CGCTTATGCC | CTCGCCTTCT | TCTACGGTGG | CATTCTCGTC | 1980 |
| AGTAACGGCC | AAGCCGACTC | CGGTATCGTC | ATCAACGTTT | TCATGTCCAT | CCTCATTGGT | 2040 |

| | | | | | |
|---|---|---|---|---|---|
| TCCTTCTCCA | TGGCGATGCT | TGCTCCCGAG | TTGGCTGCTG | TCACCAAAGC | GCGAGGCGCT | 2100 |
| GCTGCCAAGC | TTTTCGCAAC | TATCGACCGT | GTACCCGCCA | TTGATTCCGC | CAGCGAGGAA | 2160 |
| GGTTTCAAGC | CCGATGGCCT | TCGCGGTGAG | ATTAGCTTTG | AAAATGTCAA | GTTCCATTAT | 2220 |
| CCGTCCCGAC | CCAGCATTCC | TATCTTGAAG | GGCTTCACTA | CTACGTTTGA | AGCCGGTAAG | 2280 |
| ACTTTCGCTC | TCGTCGGAGC | TAGTGGAAGC | GGAAAGAGTA | CTGTCGTTTC | TCTTATTGAG | 2340 |
| AGGTTTTACG | ACCCCGTTAG | TGGTGTTGTG | AAGCTTGACG | GTAGAGATAT | CAGGTCGCTT | 2400 |
| AACCTCAATT | GGCTTCGTCA | ACAGATTGGT | ACGTATGGCT | GACTCCTATG | AGGCCCGTAT | 2460 |
| CCTGACAGTT | TTGTATAGGT | CTTGTATCTC | AGGAACCCAC | TCTTTCGGT | ACCACCGTCC | 2520 |
| GCGGTAACGT | CGAACACGGT | CTCATCGGCT | CCAGATATGA | GAATGCCTCT | CTCGAGGAAA | 2580 |
| AATTTGAGCT | TGTGAAGAAG | GCTTGTGTCG | ATGCCAACGC | CCATAATTTT | ATCATGAAAC | 2640 |
| TTCCGCAAGG | TTATGATACC | ATGGTTGGTG | AGCGCGGTAT | GCTGTTATCT | GGTGGTCAGA | 2700 |
| AGCAGCGAGT | TGCGATTGCT | CGTGCTATCG | TTTCCGACCC | TAGGATTTTG | TTGTTGGACG | 2760 |
| AAGCTACCTC | TGCTCTTGAC | ACTCAGAGCG | AAGGTATTGT | GCAAGATGCT | TTGGACAAGG | 2820 |
| CCTCGCGAGG | CAGGACTACT | ATCACCATTG | CTCATAGGTT | ATCGTAAGCG | TTCTTTGTTG | 2880 |
| CTGATTAGAA | TCATTCTCAT | TCATGTTTTT | AGTACCATTC | GAGATGCCGA | CAGAATTTAC | 2940 |
| GTGATGGGTG | GTGGCGAAGT | ACTGGAGCAG | GGTTCTCACA | ACGATCTTCT | CGCCAACGAA | 3000 |
| AACGGTCCTG | TGAGCTATTT | TTTTTTTTT | TGCCTTTTAT | GCCCCATATA | CCTGCTAATG | 3060 |
| CTTACTTCGC | TATAGTACGC | ACAACTTGTC | AACAATCAAA | AACTTGCTCA | AGAAGCTGCT | 3120 |
| GCTGAAGCCC | TCCAGGTGGA | TGACGATATC | GAGGACCCTG | ACGATGCCGT | TTTCATTGGC | 3180 |
| GGTTCTTCGC | CTATGCAAGA | AAAAGACAAA | CAGCTTCATC | GCGCAGTGAC | TGGAAGGTCT | 3240 |
| TTGGCCAGTA | TCGCCATGGA | CGACATCCAA | GCCAAGAGGG | CGGAGGAAGT | CGCAGGTGAG | 3300 |
| GACAAGATAC | CTTCAAGCTT | TGGTCTGTAT | GCCAGGCTGT | TGAGGATGAA | TTCCGCCGAT | 3360 |
| AAATTTATAT | ACATCATAGG | TGAGAATGGC | CGCTCATAGG | ATTTGACAAT | ATCAAATTGC | 3420 |
| TGAATCTTCT | GTTTAGCGT | TTATCGCCGC | CATCTGCGCA | GGCATGGTTT | ATCCTTCTTT | 3480 |
| GGCCATCCTC | TTTGGCAAAG | CCCTCTCCGA | CTTGAGATT | CAAGATCCTG | CCGAACTTCG | 3540 |
| ACATGCTCTC | AGTCGCAGTG | CGTAAGTGGT | CTTGCCTTCT | TTTTAAATTG | CATTAGCTAA | 3600 |
| CCCATGGCAT | CAGCCTGTGG | TACTTTATCA | CTGCTCTTGC | GGCTGCATTT | GTCATCTTCT | 3660 |
| TCCAAAGTGC | CGGCTTCTCT | CGCGCCGGTT | GGGATTTGAA | CGGTGTCTTG | AGAAAAAAGT | 3720 |
| TGTTCACTGC | TACTTTGCGA | CATGACATCG | AATGGTTCGA | CGAGGAACGC | AACTCTGTAA | 3780 |
| GTGACTCTCC | TTTTTTTTG | CTTTTGCCGG | GGGTGCTGAT | ATTATTCAAG | ACTGGTGCCG | 3840 |
| TCACATCCAA | CCTTGCCGAT | CAACCTCAGA | AGGTGCAAGG | TCTGTTTGGG | CCTACTTTGG | 3900 |
| GTACAGTCGT | CCAGTCCTGC | GCCACTCTCA | TCGGTGGTTG | TATTATCGGC | TTGTGCTACG | 3960 |
| GTCCTCGTAC | GTTACTTTAC | CAAGCACTGT | CTAACAATCT | AACGTTTGA | GGTAGTTCTC | 4020 |
| GCTCTGATCG | GTATCGCTTG | TATCCCCATC | CTTGTCTCTG | GAGGTTATAT | TCGTCTCAAG | 4080 |
| GTCGTTGTAC | TCAAGGACCA | ACGTATGAAG | AAGCTCCATG | CCGCTAGTGC | ACATCTTGCC | 4140 |
| AGTGAAGCTG | CTGGAGCCGT | TAAGACAGTA | GCCAGTCTTA | CCAGGGAGAA | GGATGTAAGG | 4200 |
| AGAATCTATT | CTGAAGCTCT | TAAAGCTCCT | ATGAAATTAA | ATTTGTGAGT | GCTTAAGTTT | 4260 |
| ACATCAGGAT | CCTGCTTACA | GAAAAATCAG | CCGTACTTCT | ATTAAATCCC | AGTGTCTCTT | 4320 |
| TGCGGCGAGT | CAGGGTTTGA | CTTTCTGTAT | CATTGCTCTG | GTCTTCTACA | TTGGCGCATT | 4380 |
| ATGGATCATC | GATGCCAAAT | ACTCCACTGC | TAGTTTCTAT | ACTGTCTTGA | ACTCCATTGT | 4440 |

| | | | | | |
|---|---|---|---|---|---|
| AAGTGTTTAT | TCTGTGAACC | CACTCCTTGA | CGCTAAATTT | TTCTAGGTCT | TTGCGTCTAT | 4500 |
| TCAAGCTGGA | AATGTCTTCA | CCTTCGTCCC | GGATGCGTCC | AAGGCCAATT | CCTCGGCCGC | 4560 |
| CTCCATCTTC | CGAAGCATCG | ACAATGAACC | GGCTATCAAT | GCTGAATCTA | ATGAAGGGAA | 4620 |
| GGTGCTTGAT | CACAAGCACG | TCGTTGGTCA | TGTGCGAATT | GAAGGCGTTC | ACTTCAGGTA | 4680 |
| TCCTACCAGG | CCGGGAGTGA | GAGTACTGAG | GAATTGACT | ATTGATGTTC | CTGCCGGCAC | 4740 |
| TTAGTAAGTC | AGCTCGACTG | CAGAATCTTT | TGATTTCTA | ACTCTTTTA | AGTGTGGCAC | 4800 |
| TCGTTGGTCC | TTCCGGTTGT | GGAAAGTCTA | CCACTATTCA | AATGCTGGAG | AGGTTCTACG | 4860 |
| ACCCTTTGGC | TGGCCGTGTG | ACTTTGGATG | GCATCGATAT | TAAGGAGCTC | AACTTGGCGA | 4920 |
| GTTACCGTAG | CCAGATCTCC | CTCGTTTCTC | AAGAACCTGT | AAGTAATGAG | CTAACAGGTA | 4980 |
| AGGACGTTGC | TGAATTCCTT | CTTAGACCCT | TTACGCGGGT | ACAATTAGGT | TTAATATTCT | 5040 |
| TTTGGGCGCG | AACAAGCCCA | TAGAGGAGGT | GACTCAGGAT | GAGATTGATG | CTGCCTGCAA | 5100 |
| GGATGCCAAT | ATTGTGAGTT | TAACGTCCGC | TATGGACGAG | CAATACTAAC | TTCTGCTTTA | 5160 |
| GTACGACTTT | ATCGTGTCCT | TGCCAGATGG | TTTTGACACC | GAAGTGGGTG | GGAAAGGCTC | 5220 |
| TCAGCTTTCT | GGTGGTCAAA | AGCAACGTAT | CGCTATCGCC | CGTGCTCTCA | TTCGAAACCC | 5280 |
| TAAAGTCTTG | CTCCTTGACG | AAGCTACGTC | CGCACTCGAC | AGTCAGTCAG | AAAAGGTCGT | 5340 |
| TCAGGAGGCA | CTTGATAAGG | CAGCCAAGGG | TAGAACAACC | ATTGCGATTG | CTCATCGTTT | 5400 |
| GTCGTCAATT | CAACATTCTG | ACCGGATTTA | CTACTTCTCT | GAAGGCAGGG | TAGCCGAGCA | 5460 |
| TGGAACACAT | CAGGAGCTTT | TGGCCAAGAA | GGGTGGCTAT | GTGAGTGTTC | ATCTGTCCAT | 5520 |
| TTTCATTCAC | GGGCGGTGAC | TAATTTTTGC | AGTATGAGCT | GGTTCAAATG | CAAAACCTGA | 5580 |
| GTCGTCAATA | GACAGCGCTT | GATTGAGCGT | GATCTGAAGA | TAGATTCGCA | GGAATTTAGT | 5640 |
| GTCACTGGTT | ATCAATAAGG | TTTAGTCATT | GGTATAATCT | GTCTGTAACT | TGATTTTCAT | 5700 |
| TTCAATCATT | TGCCATTCAT | GCGTTTTGAC | GCATTGCATC | TATGTACAAA | ATGTTGTCTT | 5760 |
| TACATGGCTA | AGATATCTTT | CTCAGAGACT | TAATGGCTAG | CAATGCAACA | ACTCTAGCTT | 5820 |
| TTCCTCCTTT | TAAGGCGTAA | GAAAGGGCTT | GTTGGTATTG | GTACAACAAA | AACCACAACT | 5880 |
| CTGCCACTGG | TTACTGATGA | CCAGCGGCGG | TTAAACGGTT | GAACCATGGT | AGCTAACATA | 5940 |
| TGTAAACAGC | TGAAGAAGGA | ATAATTAGCG | GTTGAAGCCT | CGCCTGATAG | CCAGTAGTTA | 6000 |
| GCCACTCAAA | AGAGGTTGTG | AATTCAGGCG | CTTGCAGTGA | ACCGAGGAGA | CCAAAAAATC | 6060 |
| AACGAGCAAC | AAGAAGTAAA | AACTCATTAC | GGCGGATGAT | GGTGGAGTGC | TTTACTTATA | 6120 |
| CAAGCTATTT | GATTGCAACT | AGT | | | | 6143 |

1

MULTIPLE DRUG RESISTANCE GENE OF CRYPTOCOCCUS NEOFORMANS

TECHNICAL FIELD OF THE INVENTION

This invention relates to recombinant DNA technology. In particular, the invention concerns the cloning of nucleic acid encoding a multiple drug resistance protein of *Cryptococcus neoformans*.

BACKGROUND OF THE INVENTION

Multiple drug resistance (MDR) mediated by the human mdr-1 gene product was initially recognized during the course of developing regimens for cancer chemotherapy (Fojo et al., 1987; *Journal of Clinical Oncology* 5: 1922–1927). A multiple drug resistant cancer cell line exhibits its resistance to high levels of a large variety of cytotoxic compounds. Frequently these cytotoxic compounds will have no common structural features nor will they interact with a common target within the cell. Resistance to these cytotoxic agents is mediated by an outward directed, ATP-dependent pump encoded by the mdr-1 gene. By this mechanism, toxic levels of a particular cytotoxic compound are not allowed to accumulate within the cell.

MDR-like genes have been identified in a number of divergent organisms including numerous bacterial species, the fruit fly *Drosophila melanogaster*, *Plasmodium falciparum*, the yeast *Saccharomyces cerevisiae*, *Caenorhabditis elegans*, *Leishmania donovanii*, marine sponges, the plant *Arabidopsis thaliana*, as well as *Homo sapiens*. Extensive searches have revealed several classes of compounds that are able to reverse the MDR phenotype of multiple drug resistant human cancer cell lines rendering them susceptible to the effects of cytotoxic compounds. These compounds, referred to herein as "MDR inhibitors", include for example, calcium channel blockers, anti-arrhythmics, antihypertensives, antibiotics, antihistamines, immuno-suppressants, steroid hormones, modified steroids, lipophilic cations, diterpenes, detergents, antidepressants, and antipsychotics (Gottesman and Pastan, 1993, *Annual Review of Biochemistry* 62: 385–427). Clinical application of human MDR inhibitors to cancer chemotherapy has become an area of intensive focus for research.

On another front, the discovery and development of antifungal compounds for specific fungal species has also met with some degree of success. Candida species represent the majority of fungal infections, and screens for new antifungal compounds have been designed to discover anti-Candida compounds. During development of antifungal agents, activity has generally been optimized based on activity against *Candida albicans*. As a consequence, these anti-Candida compounds frequently do not possess clinically significant activity against other fungal species such as *Cryptococcus neoformans*. However, it is interesting to note that at higher concentrations some anti-Candida compounds are able to kill other fungal species such as *C. neoformans*. This type of observation suggests that the antifungal target (s) of these anti-Candida compounds is present in *C. neoformans* as well. Such results indicate that *C. neoformans* may possess a natural mechanism of resistance that permits them to survive in clinically relevant concentrations of antifungal compounds. Until the present invention, such a general mechanism of resistance to antifungal compounds in *C. neoformans* has remained undescribed.

SUMMARY OF THE INVENTION

The invention provides, inter alia, isolated nucleic acid molecules that comprise nucleic acid encoding a multiple drug resistance protein from *Cryptococcus neoformans*, herein referred to as CneMDR1, vectors encoding CneMDR1, and host cells transformed with these vectors.

In another embodiment, the invention provides a method for determining the fungal MDR inhibition activity of a compound which comprises:

a) placing a culture of fungal cells, transformed with a vector capable of expressing CneMDR1, in the presence of:
   (i) an antifungal agent to which said fungal cell is resistant, but to which said fungal cell is sensitive in its untransformed state;
   (ii) a compound suspected of possessing fungal MDR inhibition activity; and
b) determining the fungal MDR inhibition activity of said compound by measuring the ability of the antifungal agent to inhibit the growth of said fungal cell.

BRIEF DESCRIPTION OF THE FIGURES

The restriction enzyme site and function maps presented in the accompanying drawings are approximate representations of plasmid pPST4 and plasmid pPST5, discussed herein. The restriction enzyme site information is not exhaustive. There may be more restriction enzyme sites of a given type on the vectors than actually shown on the maps.

DETAILED DESCRIPTION OF THE INVENTION

The present invention provides isolated nucleic acid molecules that comprise a nucleic acid sequence encoding CneMDR1. The cDNA (complementary deoxyribonucleic acid) sequence encoding CneMDR1 is provided in the Sequence Listing as SEQ ID NO: 1. The amino acid sequence of the protein encoded by CneMDR1 is provided in the Sequence Listing as SEQ ID NO: 2.

Those skilled in the art will recognize that the degenerate nature of the genetic code enables one to construct many different nucleic acid sequences that encode the amino acid sequence of SEQ ID NO: 2. The cDNA sequence depicted by SEQ ID NO: 1 is only one of many possible CneMDR1-encoding sequences. Consequently, the constructions described below and in the accompanying examples for the preferred nucleic acid molecules, vectors, and transformants of the invention are illustrative and are not intended to limit the scope of the invention.

All nucleotide and amino acid abbreviations used in this disclosure are those accepted by the United States Patent and Trademark Office as set forth in 37 C.F.R. §1.822(b)(1994).

The term "vector" refers to any autonomously replicating or integrating agent, including but not limited to plasmids, cosmids, and viruses (including phage), comprising a nucleic acid molecule to which one or more additional nucleic acid molecules can be added. Included in the definition of "vector" is the term "expression vector". Vectors are used either to amplify and/or to express deoxyribonucleic acid (DNA), either genomic or cDNA, or RNA (ribonucleic acid) which encodes CneMDR1, or to amplify DNA or RNA that hybridizes with DNA or RNA encoding CneMDR1.

The term "expression vector" refers to vectors which comprise a transcriptional promoter (hereinafter "promoter") and other regulatory sequences positioned to drive expression of a DNA segment that encodes CneMDR1. Expression vectors of the present invention are replicable DNA constructs in which a DNA sequence encoding CneMDR1 is operably linked to suitable control sequences capable of effecting the expression of CneMDR1 in a suitable host. Such control sequences include a promoter, an optional operator sequence to control transcription, a sequence encoding suitable mRNA ribosomal binding sites, and sequences which control termination of transcription and translation. DNA regions are operably linked when they are functionally related to each other. For example, a promoter is operably linked to a DNA coding sequence if it controls the transcription of the sequence, or a ribosome binding site is operably linked to a coding sequence if it is positioned so as to permit translation.

The term "MDR inhibition activity" refers to the ability of a compound to inhibit the MDR activity of a host cell, thereby increasing the antifungal activity of an antifungal compound against said host cell.

In the present invention, CneMDR1 may be synthesized by host cells transformed with vectors that provide for the expression of DNA encoding CneMDR1. The DNA encoding CneMDR1 may be the natural sequence or a synthetic sequence or a combination of both ("semi-synthetic sequence"). The in vitro or in vivo transcription and translation of these sequences results in the production of CneMDR1. Synthetic and semi-synthetic sequences encoding CneMDR1 may be constructed by techniques well known in the art. See Brown et al. (1979) *Methods in Enzymology*, Academic Press, N.Y., 68: 109–151. CneMDR1-encoding DNA, or portions thereof, may be generated using a conventional DNA synthesizing apparatus such as the Applied Biosystems Model 380A, 380B, 394 or 3948 DNA synthesizers (commercially available from Applied Biosystems, Inc., 850 Lincoln Center Drive, Foster City, Calif. 94404).

Owing to the natural degeneracy of the genetic code, the skilled artisan will recognize that a sizable yet definite number of nucleic acid sequences may be constructed which encode CneMDR1. All such nucleic acid sequences are provided by the present invention. These sequences can be prepared by a variety of methods and, therefore, the invention is not limited to any particular preparation means. The nucleic acid sequences of the invention can be produced by a number of procedures, including DNA synthesis, cDNA cloning, genomic cloning, polymerase chain reaction (PCR) technology, or a combination of these approaches. These and other techniques are described by Maniatis, et al., *Molecular Cloning: A Laboratory Manual*, Cold Spring Harbor Press, Cold Spring Harbor Laboratory, Cold Spring Harbor, N.Y. (1989), or *Current Protocols in Molecular Biology* (F. M. Ausubel et al., 1989 and supplements). The contents of both of these references are incorporated herein by reference.

Figure 1:
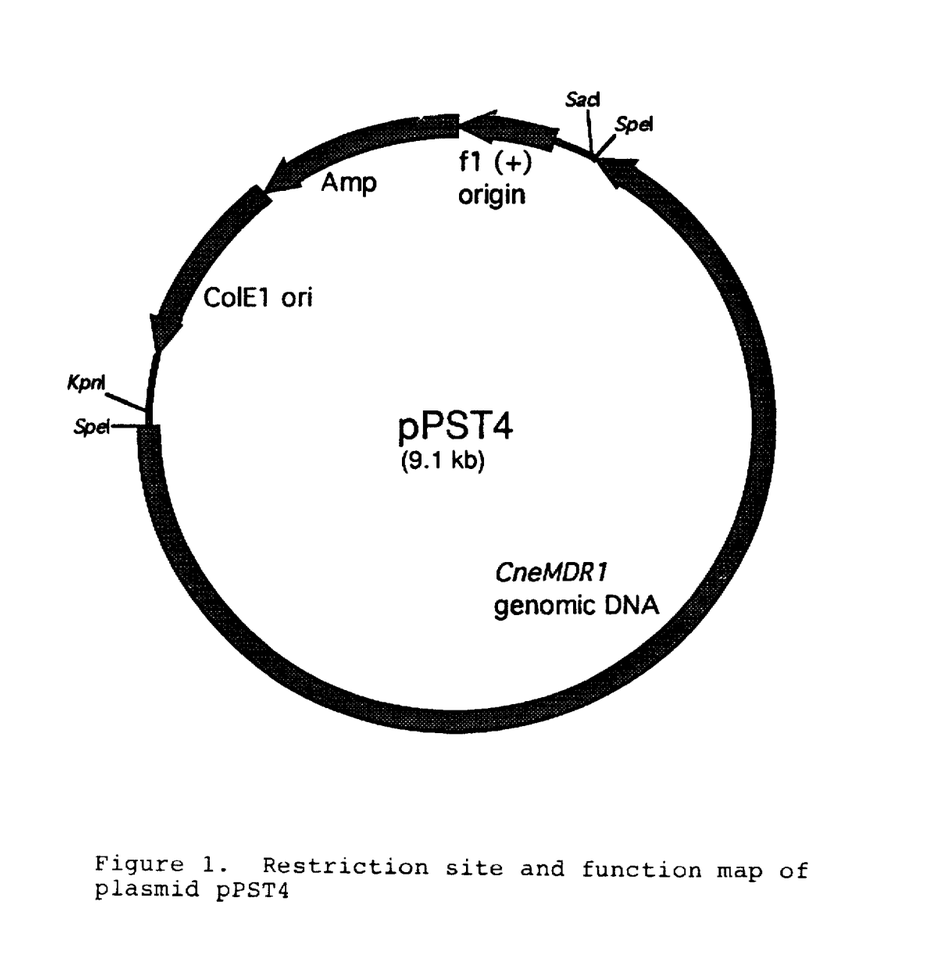
FIG. 1—A restriction enzyme site and function map of plasmid pPST4.

In another aspect, this invention provides the genomic DNA encoding CneMDR1, which may be obtained by synthesizing the desired portion of SEQ ID No. 3 or by following the procedure carried out by Applicants. The entire open reading frame encoding CneMDR1 plus introns is contained within an approximately 6.1 kb SpeI restriction fragment. The exons in SEQ ID No. 3 are at nucleotides 541–1072, 1130–1395, 1443–1872, 1925–2428, 2479–2863, 2913–3009, 3076–3379, 3438–3561, 3614–3776, 3831–3966, 4016–4244, 4291–4438, 4487–4743, 4793–4958, 5006–5113, 5162–5500, and 5553–5591 (includes the stop codon). This fragment may be obtained in the following manner. If a different strain of *Cryptococcus neoformans* (M1-106, obtained from the Indiana Board of Health) is used than the one Applicants used some adjustment may need to be made in what restriction sites are used to isolate the final fragment. Applicants used Total DNA isolated from *Cryptococcus neoformans* digested with the restriction enzyme SpeI. The DNA fragments produced by this digestion were separated in a 0.8% agarose gel. That region of the gel containing DNA fragments in the 5.5 to 6.5 kb range was excised and the DNA contained therein was recovered by electroelution. The isolated SpeI DNA restriction fragments were then ligated into pBluescript II KS[+] (Stratagene, Inc.) which was cut with SpeI. Transformants containing recombinant plasmids with the size selected inserts were screened by hybridization with a radiolabeled probe designed to detect CneMDR1. An approximately 230 base pair CneMDR1 radiolabeled probe was produced by PCR using the following primers: 5'-CAGAAGTTAGTATTGCTCGTCC-3' and 5'-GAGCTCAACTTGGCGAGTTACC-3' and the above genomic DNA as a template in the presence of $^{32}$P-radiolabeled nucleotides. A plasmid designated pPST4 was isolated which contains the complete genomic sequence of CneMDR1 within the approximately 6.1 kb SpeI restriction fragment. A restriction site and function map of pPST4 is provided as FIG. 1 of the drawings. Plasmid pPST4 comprises the ColE1 origin of replication (ColE1) which allows replication in *Escherichia coli* host cells, and the ampicillin resistance gene (Amp) for selection of *E. coli* cells transformed with the plasmid grown in the presence of ampicillin. The plasmid also contains the origin of replication from the f1 filamentous phage. The genomic DNA encoding CneMDR1 can be obtained from plasmid pPST4 on an approximately 6.1 kilobase pair SpeI restriction enzyme fragment.

To effect the translation of CneMDR1-encoding mRNA, one inserts the natural, synthetic, or semi-synthetic CneMDR1-encoding DNA sequence into any of a large number of appropriate expression vectors through the use of appropriate restriction endonucleases and DNA ligases. Synthetic and semi-synthetic CneMDR1-encoding DNA sequences can be designed, and natural CneMDR1-encoding nucleic acid can be modified, to possess restriction endonuclease cleavage sites to facilitate isolation from and integration into these vectors. Particular restriction endonucleases employed will be dictated by the restriction endonuclease cleavage pattern of the expression vector utilized. Restriction enzyme sites are chosen so as to properly orient the CneMDR1-encoding DNA with the control sequences to achieve proper in-frame transcription and translation of the CneMDR1 molecule. The CneMDR1-encoding DNA must be positioned so as to be in proper reading frame with the promoter and ribosome binding site of the expression vector, both of which are functional in the host cell in which CneMDR1 is to be expressed.

Expression of CneMDR1 in fungal cells, such as *Saccharomyces cerevisiae* is preferred. Suitable promoter sequences for use with yeast hosts include the promoters for 3-phosphoglycerate kinase (found on plasmid pAP12BD (ATCC 53231) and described in U.S. Pat. No. 4,935,350, Jun. 19, 1990) or other glycolytic enzymes such as enolase (found on plasmid pAC1 (ATCC 39532)), glyceraldehyde-3-phosphate dehydrogenase (derived from plasmid pHc-GAPC1 (ATCC 57090, 57091)), hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Inducible yeast promoters have the additional advantage of transcription controlled by growth conditions. Such promoters include the promoter regions for alcohol dehydrogenase 2, isocytochrome C, acid phosphotase, degradative enzymes associated with nitrogen metabolism, metallothionein (contained on plasmid vector pCL28XhoLHBPV (ATCC 39475), U.S. Pat. No. 4,840, 896), glyceraldehyde 3-phosphate dehydrogenase, and enzymes responsible for maltose and galactose utilization (GAL1 found on plasmid pRY121 (ATCC 37658) and on plasmid pPST5, described below). Suitable vectors and promoters for use in yeast expression are further described by R. Hitzeman et al., in European Patent Publication No. 73,657A. Yeast enhancers such as the UAS Gal enhancer from *Saccharomyces cerevisiae* (found in conjunction with the CYC1 promoter on plasmid YEpsec—hI1beta, ATCC 67024), also are advantageously used with yeast promoters.

A variety of expression vectors useful in the present invention are well known in the art. For expression in Saccharomyces, the plasmid YRp7, for example, (ATCC-40053, Stinchcomb et al., 1979, *Nature* 282: 39; Kingsman et al., 1979, *Gene* 7: 141 ; Tschemper et al., 1980, *Gene* 10: 157) is commonly used. This plasmid contains the trp gene which provides a selection marker for a mutant strain of yeast lacking the ability to grow in tryptophan, for example ATCC 44076 or PEP4-1 (Jones, 1977, *Genetics* 85: 12).

Expression vectors useful in the expression of CneMDR1 can be constructed by a number of methods. For example, the CDNA sequence encoding CneMDR1 can be synthesized using DNA synthesis techniques such as those described above. Such synthetic DNA can be synthesized to contain cohesive ends that allow facile cloning into an appropriately digested expression vector. For example, the cDNA encoding CneMDR1 can be synthesized to contain NotI cohesive ends. Such a synthetic DNA fragment can be ligated into a NotI-digested expression vector such as pYES-2 (Invitrogen Corp., San Diego Calif. 92121). The resultant plasmid is designated herein as pPST5. Plasmid pPST5 is useful for the expression of CneMDR1 in *Saccharomyces cerevisiae*.

Plasmid pPST5 can also be constructed in the following manner. Logarithmic phase *Cryptococcus neoformans* cells are disrupted by grinding under liquid nitrogen according to the procedure of minuth et al., 1982 (*Current Genetics* 5: 227–231). *Cryptococcus neoformans* mRNA is preferably isolated from the disrupted cells using the QuickPrep® mRNA Purification Kit (Pharmacia Biotech) according to the instructions of the manufacturer. cDNA is produced from the isolated mRNA using the TimeSaver® cDNA Synthesis Kit (Pharmacia Biotech) using oligo (dT) according to the procedure described by the manufacturer. In this process an EcoRI/NotI adapter (Stratagene, Inc.) is ligated to each end of the double stranded cDNA. The adapter modified cDNA is ligated into the vector Lambda Zap$^R$II® using the Predigested Lambda Zap$^R$II®/EcoRI/CIAP Cloning Kit (Stratagene, Inc.) according to the instructions of the manufacturer to create a cDNA library.

The library is screened for full-length cDNA encoding CneMDR1 using a $^{32}$P-radiolabeled fragment of the CneMDR1 gene. This radiolabeled fragment is produced from the CneMDR1 genomic DNA present in plasmid pPST4 and is used as template. Utilizing the polymerase chain reaction (Gene Amp® Kit, Perkin Elmer Cetus, Norwalk, Conn.) and the following primers: 5'-CAGAAGTTAGTATTGCTCGTCC-3' and 5'-GAGCTCAACTTGGCGAGTTACC-3' in the presence of $^{32}$P-radiolabeled nucleotide, an approximately 230 base pair CneMDR1 radiolabeled DNA fragment is obtained.

This radiolabeled fragment is used to probe the *Cryptococcus neoformans* cDNA library using standard hybridization techniques (Maniatis et al. 1992). In this manner, a full-length cDNA clone is recovered from the *Cryptococcus neoformans* cDNA library. A full-length cDNA clone recovered from the library is removed from the Lambda Zap$^R$II® vector by digestion with the restriction endonuclease NotI which produces an approximately 4100 base pair DNA fragment encoding CneMDR1. The vector DNA fragment and the desired approximately 4100 base pair NotI DNA restriction fragment are separated by agarose gel electrophoresis. The desired approximately 4100 base pair NotI DNA fragment encoding CneMDR1 is isolated by cutting out that portion of the agarose gel containing the fragment and electroeluting the DNA using a Centrilutor™ Microelectroeluter (Amicon, Inc.) according to the manufacturer's instructions. The isolated approximately 4100 base pair NotI restriction fragment encoding CneMDR1 is ligated to NotI digested pYES2 vector DNA. The correct orientation of the insert DNA is screened for by restriction endonuclease digestion using asymmetric sites located within the coding region and the flanking vector. The resultant plasmid, pPST5, is useful for the expression of CneMDR1 in *Saccharomyces cerevisiae*.

Figure 2:
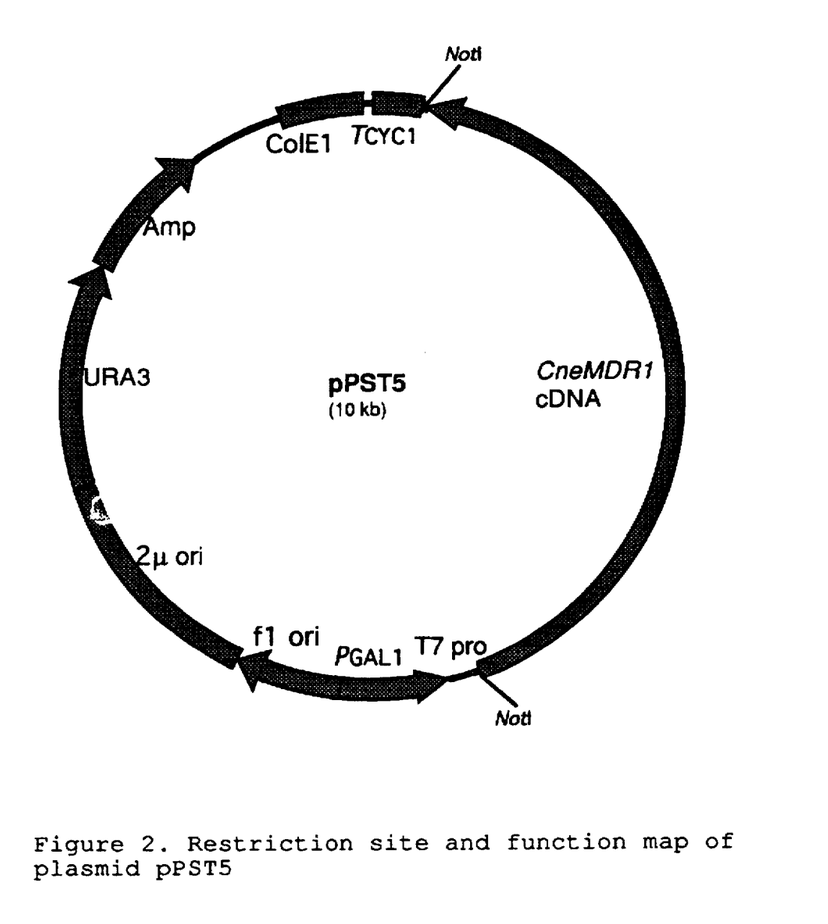
FIG. 2—A restriction enzyme site and function map of plasmid pPST5.

A representation of plasmid pPST5 is provided as FIG. 2. As noted above, this plasmid contains the CneMDR1-encoding DNA operably linked to the *Saccharomyces cerevisiae* GAL1 promoter (P Gal1). Plasmid pPST5 also comprises the yeast transcription terminator cyc1 (T cyc1) located in a position 3' to the CneMDR1-encoding DNA. Plasmid pPST5 further comprises the ColE1 origin of replication (ColE1) which allows replication in *Escherichia coli* host cells, and the ampicillin resistance gene (Amp) for selection of *E. coli* cells transformed with the plasmid grown in the presence of ampicillin. Plasmid pPST5 further comprises the yeast 2μ origin of replication (2μ ori) allowing replication in yeast host cells, the yeast URA3 gene for selection of *S. cerevisiae* cells transformed with the plasmid grown in a medium lacking uracil, and the origin of replication from the f1 filamentous phage.

In a preferred embodiment of the invention *Saccharomyces cerevisiae* INVSc1 or INVSc2 cells (Invitrogen Corp., Sorrento Valley Blvd., San Diego Calif. 92121) are employed as host cells, but numerous other cell lines are available for this use. The transformed host cells are plated on an appropriate medium under selective pressure (minimal medium lacking uracil). The cultures are then incubated for a time and temperature appropriate to the host cell line employed.

The techniques involved in the transformation of yeast cells such as *Saccharomyces cerevisiae* cells are well known in the art and may be found in such general references as Ausubel et al., *Current Protocols in Molecular Biology* (1989), John Wiley & Sons, New York, N.Y. and supplements. The precise conditions under which the transformed yeast cells are cultured is dependent upon the nature of the yeast host cell line and the vectors employed.

Nucleic acid, either RNA or DNA, which encodes CneMDR1, or a portion thereof, is also useful in producing nucleic acid molecules useful in diagnostic assays for the detection of CneMDR1 mRNA, CneMDR1 cDNA, or CneMDR1 genomic DNA. Further, nucleic acid, either RNA or DNA, which does not encode CneMDR1, but which nonetheless is capable of hybridizing with CneMDR1-encoding DNA or RNA is also useful in such diagnostic assays. These nucleic acid molecules may be covalently labeled by known methods with a detectable moiety such as a fluorescent group, a radioactive atom or a chemiluminescent group. The labeled nucleic acid is then used in conventional hybridization assays, such as Southern or Northern hybridization assays, or polymerase chain reaction assays (PCR), to identify hybridizing DNA, cDNA, or RNA molecules. PCR assays may also be performed using unlabeled nucleic acid molecules. Such assays may be employed to identify CneMDR1 vectors and transformants and in in vitro diagnosis to detect CneMDR1-like mRNA, cDNA, or genomic DNA from other organisms.

U.S. patent application Ser. No. 08/111680, the entire contents of which are hereby incorporated herein by reference, describes the use of combination therapy involving an antifungal agent possessing a proven spectrum of activity, with a fungal MDR inhibitor to treat fungal infections. This combination therapy approach enables an extension of the spectrum of antifungal activity for a given antifungal compound which previously had only demonstrated limited clinically relevant antifungal activity. Similarly, compounds with demonstrated antifungal activity can also be potentiated by a fungal MDR inhibitor such that the antifungal activity of these compounds is extended to previously resistant species. To identify compounds useful in such combination therapy the present invention provides an assay method for identifying compounds with *Cryptococcus neoformans* MDR inhibition activity. Host cells that express CneMDR1 provide an excellent means for the identification of compounds useful as inhibitors of *Cryptococcus neoformans* MDR activity. Generally, the assay utilizes a culture of a yeast cell transformed with a vector which provides expression of CneMDR1. The expression of CneMDR1 by the host cell enables the host cell to grow in the presence of an antifungal compound to which the yeast cell is sensitive to in the untransformed state. Thus, the transformed yeast cell culture is grown in the presence of i) an antifungal agent to which the untransformed yeast cell is sensitive, but to which the transformed host cell is resistant, and ii) a compound that is suspected of being an MDR inhibitor. The effect of the suspected MDR inhibitor is measured by testing for the ability of the antifungal compound to inhibit the growth of the transformed yeast cell. Such inhibition will occur if the suspected *Cryptococcus neoformans* MDR inhibitor blocks the ability of CneMDR1 to prevent the antifungal compound from acting on the yeast cell. An illustrative example of such an assay is provided in Example 3.

In order to illustrate more fully the operation of this invention, the following examples are provided, but are not to be construed as a limitation on the scope of the invention.

EXAMPLE 1
Source of the CneMDR1-Encodina Genomic DNA and CDNA of *Cryptococcus neoformans*

Genomic DNA encoding CneMDR1 (sequence presented in SEQ ID NO: 3) or the corresponding cDNA sequence (presented in SEQ ID NO: 1) may be from a natural sequence, a synthetic source or a combination of both ("semi-synthetic sequence"). The in vitro or in vivo transcription and translation of these sequences results in the production of CneMDR1. Synthetic and semi-synthetic sequences encoding CneMDR1 may be constructed by techniques well known in the art. See Brown et al. (1979) *Methods in Enzymology*, Academic Press, N.Y., 68: 109–151. CneMDR1-encoding DNA, or portions thereof, may be generated using a conventional DNA synthesizing apparatus such as the Applied Biosystems Model 380A, 380B, 384 or 3848 DNA synthesizers (commercially available from Applied Biosystems, Inc., 850 Lincoln Center Drive, Foster City, Calif. 94404). The polymerase chain reaction is especially useful in generating these DNA sequences. PCR primers are constructed which include the translational start (ATG) and translational stop codon (TAG) of CneMDR1. Restriction enzyme sites may be included on these PCR primers outside of the CneMDR1 coding region to facilitate rapid cloning into expression vectors. *Cryptococcus neoformans* genomic DNA is used as the PCR template for synthesis of CneMDR1 including introns which is useful for expression studies in closely related fungi. In contrast, cDNA is used as the PCR template for synthesis of CneMDR1 devoid of introns which is useful for expression in foreign hosts such as Saccharomyces cerevisiae or bacterial hosts such as *Escherichia coli*.

EXAMPLE 2
Expression of the CneMDR1 Protein

*Saccharomyces cerevisiae* INVSc1 cells (Invitrogen Corp., San Diego Calif. 92191) are transformed with the plasmid pPST5 by the technique described by J. D. Beggs, 1988, *Nature* 275: 104–109). The transformed yeast cells are grown in a broth medium containing YNB/CSM-Ura/raf (YNB/CSM-Ura [Yeast Nitrogen Base (Difco Laboratories, Detroit, Mich.) supplemented with CSM-URA (Bio 101, Inc.)] supplemented with 4% raffinose) at 28° C. in a shaker incubator until the culture is saturated. To induce expression of CneMDR1, a portion of the culture is used to inoculate a flask containing YNB/CSM-Ura medium supplemented with 2% galactose (YNB/CSM-Ura/gal) rather than raffinose as the sole carbon source. The inoculated flask is incubated at 28° C. for about 16 hours.

EXAMPLE 3
Antifungal Potentiator Assay

Approximately $1\times10^6$ cells of a *Saccharomyces cerevisiae* INVSc1/pPST5 culture are delivered to each of several agar plates containing YNB/CSM-Ura/gal. The agar surface is allowed to dry in a biohazard hood. *Saccharomyces cerevisiae* INVSc1/pPST5 cells express the CneMDR1 activity.

An antifungal compound that the untransformed yeast cell is typically sensitive to is dissolved in an appropriate solvent at a concentration that is biologically effective. Twenty µl of the solution is delivered to an antibiotic susceptibility test disc (Difco Laboratories, Detroit, Mich.). After addition of the antifungal solution the disc is allowed to air dry in a biohazard hood. When dry, the disc is placed on the surface of the petri plates containing the *Saccharomyces cerevisiae* INVSc1/pPST5 cells.

Compounds to be tested for the ability to inhibit CneMDR1 are dissolved in dimethylsulfoxide (DMSO). The amount of compound added to the DMSO depends on the solubility of the individual compound to be tested. Twenty µl of the suspensions containing a compound to be tested are delivered to an antibiotic susceptibility test disc (Difco Laboratories, Detroit, Mich.). The disc is then placed on the surface of the dried petri plates containing the *Saccharomyces cerevisiae* INVSc1/pPST5 cells approximately 2 cm from the antifungal-containing disc. Petri plates containing the two discs are incubated at 28° C. for about 16–48 hours.

Following this incubation period, the petri plates are examined for zones of growth inhibition around the discs. A zone of growth inhibition near the antifungal disc on the test plate indicates that the compound being tested for MDR inhibition activity blocks the activity of CneMDR1 and allows the antifungal compound to inhibit the growth of the yeast host cell. Such compounds are said to possess MDR inhibition activity. Little or no zone of growth inhibition indicates that the test compound does not block MDR activity and, thus, CneMDR1 is allowed to act upon the antifungal compound to prevent its activity upon the host cell.

---

We claim:

1. A DNA compound that comprises an isolated DNA sequence encoding SEQ ID NO: 2.

2. The DNA compound of claim 1 which comprises the isolated DNA sequence which is SEQ ID NO: 1.

3. The DNA compound of claim 1 which comprises the isolated DNA sequence which is SEQ ID NO: 3.

4. A vector comprising the isolated DNA sequence of claim 1.

5. A vector comprising the isolated DNA sequence of claim 2.

6. A vector comprising the isolated DNA sequence of claim 3.

7. A method for constructing a transformed host cell which expresses SEQ ID NO: 2, said method comprising transforming a host cell with a recombinant DNA vector that comprises the isolated DNA sequence of claim 1.

8. A method for expressing SEQ ID NO: 2 in a transformed host cell; said method comprising culturing said transformed host cell of claim 7 under conditions suitable for gene expression.

9. A host cell containing the vector of claim 4.

10. A host cell containing the vector of claim 5.

11. A host cell containing the vector of claim 6.

* * * * *